(12) United States Patent
Falsafi et al.

(10) Patent No.: US 7,632,098 B2
(45) Date of Patent: Dec. 15, 2009

(54) SELF-ADHESIVE DENTAL COMPOSITIONS AND METHODS

(75) Inventors: Afshin Falsafi, Woodbury, MN (US); Steven M. Aasen, Woodbury, MN (US); Ahmed S. Abuelyaman, Woodbury, MN (US); David K. Cinader, Yorba Linda, CA (US); Bradley D. Craig, Cottage Grove, MN (US); Reinhold Hecht, Kaufering (DE); Thomas Luchterhandt, Greifenberg (DE); Sumita B. Mitra, West St. Paul, MN (US); Joel D. Oxman, Minneapolis, MN (US); Prabhakara S. Rao, Maplewood, MN (US); Brian A. Shukla, St. Paul, MN (US); Markus Watermann, Inning am Ammersee (DE)

(73) Assignee: 3M Innovative Properties Company, St. Paul, MN (US)

( * ) Notice: Subject to any disclaimer, the term of this patent is extended or adjusted under 35 U.S.C. 154(b) by 236 days.

(21) Appl. No.: 10/916,240

(22) Filed: Aug. 11, 2004

(65) Prior Publication Data

US 2005/0175966 A1 Aug. 11, 2005

Related U.S. Application Data

(60) Provisional application No. 60/494,603, filed on Aug. 12, 2003.

(51) Int. Cl.
*A61C 5/00* (2006.01)
*A61C 3/00* (2006.01)
(52) U.S. Cl. .................... 433/215; 433/24; 433/226
(58) Field of Classification Search ............... 433/215, 433/24, 222.1, 223, 226, 228.1, 9
See application file for complete search history.

(56) References Cited

U.S. PATENT DOCUMENTS

| | | | |
|---|---|---|---|
| 4,054,598 A | 10/1977 | Blum et al. | 260/502 |
| 4,070,321 A | 1/1978 | Goretta et al. | 260/296 |
| 4,204,978 A | 5/1980 | Ibsen et al. | |
| 4,259,075 A | 3/1981 | Yamauchi et al. | |
| 4,259,117 A | 3/1981 | Yamauchi et al. | |
| 4,267,108 A | 5/1981 | Blum et al. | 260/326 |
| 4,298,738 A | 11/1981 | Lechtken et al. | |
| 4,302,381 A | 11/1981 | Omura et al. | |
| 4,304,734 A | 12/1981 | Jary et al. | 260/502 |
| 4,324,744 A | 4/1982 | Lechtken et al. | |
| 4,327,039 A | 4/1982 | Blum et al. | 260/502 |
| 4,356,296 A | 10/1982 | Griffith et al. | |
| 4,368,403 A | 1/1983 | Lewis | |
| 4,376,835 A | 3/1983 | Schmitt et al. | |
| 4,383,052 A | 5/1983 | Higo et al. | 523/118 |
| 4,385,109 A | 5/1983 | Lechtken et al. | |
| 4,407,761 A | 10/1983 | Blum et al. | 260/502 |
| 4,499,251 A | 2/1985 | Omura et al. | |
| 4,503,169 A | 3/1985 | Randklev | |
| 4,526,728 A | 7/1985 | Finke et al. | 260/502 |
| 4,537,940 A | 8/1985 | Omura et al. | |
| 4,539,382 A | 9/1985 | Omura et al. | |
| 4,612,384 A | 9/1986 | Omura et al. | |
| 4,621,077 A | 11/1986 | Rosini et al. | 514/108 |
| 4,642,126 A | 2/1987 | Zador et al. | |
| 4,648,843 A | 3/1987 | Mitra | |
| 4,650,847 A | 3/1987 | Omura et al. | |
| 4,652,274 A | 3/1987 | Boettcher et al. | |
| 4,665,217 A | 5/1987 | Reiners et al. | |
| 4,687,767 A | 8/1987 | Bosies et al. | 514/89 |
| 4,695,251 A | 9/1987 | Randklev | |
| 4,710,523 A | 12/1987 | Lechtken et al. | |
| 4,719,149 A | 1/1988 | Aasen et al. | |
| 4,737,593 A | 4/1988 | Ellrich et al. | |
| 4,752,338 A | 6/1988 | Reiners et al. | |
| 4,755,620 A | 7/1988 | Iwamoto et al. | |
| 4,792,632 A | 12/1988 | Ellrich et al. | |
| 4,814,514 A | 3/1989 | Yokota et al. | |
| 4,872,936 A | 10/1989 | Engelbrecht | |
| 4,922,007 A | 5/1990 | Kieczykowski et al. | 562/13 |
| 4,939,283 A | 7/1990 | Yokota et al. | |
| 5,019,651 A | 5/1991 | Kieczykowski | 562/13 |
| 5,026,902 A | 6/1991 | Fock et al. | |
| 5,055,497 A | 10/1991 | Okada et al. | |
| 5,063,257 A | 11/1991 | Akahane et al. | 523/116 |

(Continued)

FOREIGN PATENT DOCUMENTS

DE 2 537 463 4/1976

(Continued)

OTHER PUBLICATIONS

Banerjee et al., *Ind. Eng. Chem. Res.*, vol. 35, No. 9, pp. 3100-3107 "Polymer Precipitation Using a Micellar Nonsolvent: The Role of Surfactant—Polymer Interactions and the Development of a Microencapsulation Technique", (1996).
Buonocore et al., *J. Dent. Res.*, vol. 35, No. 6, pp. 846-851, "A Report on a Resin Composition Capable of Bonding to Human Dentin Surfaces", (1956).
Floyd Green, The Sigma-Aldrich Handbook of Stains, Dyes, & Indicators [with/Transmission Spectrum Reference], Aldrich Chem. Co., Milwaukee, WI (1990).
Holmberg et al., "Microemulsions," Chapter 6, *Surfactants and Polymers in Aqueous Solution*, Second Edition, John Wiley & Sons, pp. 138-155 (2003; Reprinted with corrections in 2004).
ISO Standard 4049:2000.
ISO Standard 7489.
ISO Standard 9917-1:2003.

(Continued)

*Primary Examiner*—John J Wilson

(57) ABSTRACT

The present invention is directed to dental compositions that can be used as adhesives for bonding a dental material to a dental structure surface and/or as a dental restorative material. The dental composition is preferably applied to a dental structure surface under conditions effective to etch the dental structure surface.

12 Claims, No Drawings

U.S. PATENT DOCUMENTS

| | | | |
|---|---|---|---|
| 5,076,844 A | 12/1991 | Fock et al. | |
| 5,130,347 A | 7/1992 | Mitra | |
| 5,154,762 A | 10/1992 | Mitra et al. | |
| 5,180,757 A | 1/1993 | Lucey | 522/76 |
| 5,227,413 A | 7/1993 | Mitra | 523/116 |
| 5,254,198 A | 10/1993 | Kawashima et al. | |
| 5,256,447 A | 10/1993 | Oxman et al. | |
| 5,324,862 A | 6/1994 | Yokota et al. | |
| 5,332,854 A | 7/1994 | Yokota et al. | |
| 5,354,827 A | 10/1994 | Müller et al. | 526/304 |
| 5,367,002 A | 11/1994 | Huang et al. | 523/116 |
| 5,501,727 A | 3/1996 | Wang et al. | |
| 5,510,517 A | 4/1996 | Dauer et al. | 562/13 |
| 5,520,725 A | 5/1996 | Kato et al. | 106/35 |
| 5,525,648 A | 6/1996 | Aasen et al. | |
| 5,530,038 A | 6/1996 | Yamamoto et al. | |
| 5,545,676 A | 8/1996 | Palazzotto et al. | |
| 5,554,030 A | 9/1996 | Ario et al. | 433/226 |
| 5,629,361 A | 5/1997 | Nakabayashi et al. | 523/118 |
| 5,648,491 A | 7/1997 | Dauer et al. | 546/22 |
| 5,658,963 A | 8/1997 | Qian et al. | |
| 5,710,194 A | 1/1998 | Hammesfahr et al. | |
| 5,766,012 A | 6/1998 | Rosenbaum et al. | |
| 5,834,532 A | 11/1998 | Yamamoto et al. | |
| 5,859,089 A | 1/1999 | Qian | 523/116 |
| 5,871,360 A | 2/1999 | Kato | 433/226 |
| 5,925,715 A | 7/1999 | Mitra | 525/293 |
| 5,962,550 A | 10/1999 | Akahane et al. | 523/116 |
| 5,965,632 A | 10/1999 | Orlowski et al. | 523/116 |
| 5,980,253 A | 11/1999 | Oxman et al. | 433/228 |
| 6,004,390 A | 12/1999 | Pflug et al. | |
| 6,030,606 A | 2/2000 | Holmes | |
| 6,050,815 A * | 4/2000 | Adam et al. | 433/9 |
| 6,172,131 B1 | 1/2001 | Moszner et al. | 523/116 |
| 6,251,963 B1 | 6/2001 | Köhler et al. | |
| 6,306,926 B1 | 10/2001 | Bretscher et al. | 523/116 |
| 6,309,215 B1 | 10/2001 | Phan et al. | |
| 6,331,080 B1 | 12/2001 | Cole et al. | |
| 6,350,839 B2 | 2/2002 | Moszner et al. | 526/278 |
| 6,387,979 B1 * | 5/2002 | Hino | 523/116 |
| 6,387,981 B1 | 5/2002 | Zhang et al. | |
| 6,387,982 B1 | 5/2002 | Blackwell | |
| 6,444,725 B1 | 9/2002 | Trom et al. | |
| 6,458,868 B1 | 10/2002 | Okada et al. | |
| 6,472,454 B1 * | 10/2002 | Qian | 523/116 |
| 6,482,871 B1 | 11/2002 | Aasen et al. | |
| 6,506,816 B1 | 1/2003 | Ario et al. | |
| 6,528,555 B1 | 3/2003 | Nikutowski et al. | |
| 6,565,873 B1 | 5/2003 | Shefer et al. | 424/426 |
| 6,566,413 B1 | 5/2003 | Weinmann et al. | |
| 6,572,693 B1 | 6/2003 | Wu et al. | |
| 6,624,236 B1 | 9/2003 | Bissinger et al. | |
| 6,691,715 B2 | 2/2004 | Matz et al. | 132/202 |
| 7,129,281 B2 * | 10/2006 | Fujiwara | 522/153 |
| 2001/0044513 A1 | 11/2001 | Moszner et al. | 526/278 |
| 2002/0015682 A1 | 2/2002 | Stangel et al. | |
| 2002/0016384 A1 | 2/2002 | Moszner et al. | 523/115 |
| 2003/0087986 A1 | 5/2003 | Mitra | 523/116 |
| 2003/0166737 A1 | 9/2003 | Dede et al. | |
| 2003/0166740 A1 | 9/2003 | Mitra et al. | |
| 2003/0166816 A1 | 9/2003 | Bissinger et al. | 528/10 |
| 2003/0181541 A1 | 9/2003 | Wu et al. | |
| 2003/0187092 A1 | 10/2003 | Fujiwara | |
| 2003/0195273 A1 | 10/2003 | Mitra et al. | |
| 2004/0110864 A1* | 6/2004 | Hecht et al. | 523/113 |
| 2004/0206932 A1 | 10/2004 | Abuelyaman | |

FOREIGN PATENT DOCUMENTS

| | | |
|---|---|---|
| DE | 35 36076 A1 | 4/1987 |
| DE | 273 846 | 11/1989 |
| DE | 199 18 974 | 12/1999 |
| DE | 695 18 037 T2 | 3/2001 |
| EP | 0 115 812 A2 | 8/1984 |
| EP | 0 115 948 A1 | 8/1984 |
| EP | 0 173 567 A2 | 3/1986 |
| EP | 0 184 095 A2 | 6/1986 |
| EP | 0 115 948 B1 | 10/1986 |
| EP | 0 201 031 A2 | 11/1986 |
| EP | 0 201 778 A1 | 11/1986 |
| EP | 0 206 810 A2 | 12/1986 |
| EP | 0 237 233 A2 | 9/1987 |
| EP | 0 201 778 B1 | 12/1988 |
| EP | 0 184 095 B1 | 7/1989 |
| EP | 0 201 031 B1 | 8/1989 |
| EP | 0 335 645 A3 | 10/1989 |
| EP | 0 355 645 A2 | 10/1989 |
| EP | 0 351 076 A2 | 1/1990 |
| EP | 0 206 810 B1 | 4/1990 |
| EP | 0 373 384 A1 | 6/1990 |
| EP | 2 251 861 A | 7/1992 |
| EP | 0 335 645 B1 | 8/1992 |
| EP | 0 373 384 B1 | 10/1992 |
| EP | 0 509 516 A2 | 10/1992 |
| EP | 0 509 516 A3 | 10/1992 |
| EP | 0 537 774 A1 | 4/1993 |
| EP | 0 351 076 B1 | 8/1993 |
| EP | 0 661 034 A1 | 7/1995 |
| EP | 0 712 622 A1 | 5/1996 |
| EP | 0 509 516 B1 | 3/1997 |
| EP | 0 537 774 B1 | 1/1998 |
| EP | 0 661 034 B1 | 3/1999 |
| EP | 0 712 622 B1 | 9/1999 |
| EP | 1 051 961 A1 | 11/2000 |
| EP | 1 141 094 | 10/2001 |
| EP | 1 287 805 A1 | 3/2003 |
| EP | 1 346 717 A1 | 9/2003 |
| WO | WO 98/46198 A1 | 10/1998 |
| WO | WO 00/30591 A1 | 6/2000 |
| WO | WO 00/38619 A2 | 7/2000 |
| WO | WO 00/38619 A3 | 7/2000 |
| WO | WO 00/42092 A1 | 7/2000 |
| WO | WO 01/07444 A1 | 2/2001 |
| WO | WO 01/30304 | 5/2001 |
| WO | WO 01/30305 A1 | 5/2001 |
| WO | WO 01/30306 A1 | 5/2001 |
| WO | WO 01/30307 A1 | 5/2001 |
| WO | WO 01/92271 A1 | 12/2001 |
| WO | WO 02/02057 | 1/2002 |
| WO | WO 02/092021 A1 | 11/2002 |
| WO | WO 03/013444 A1 | 2/2003 |
| WO | WO 03/063804 A1 | 8/2003 |
| WO | WO 03/068174 | 8/2003 |
| WO | WO 2006/014597 | 2/2006 |

OTHER PUBLICATIONS

Leung et al., "Ch. 9, Microemulsions: Formation, Structure, Properties, and Novel Applications," *Surfactants in Chemical/Processing Engineering*, Marcel Dekker, Inc., New York and Basel, Title page, Publication page, and pp. 315-367(1988).

Ostrovosky et al., "Mechanism of Microemulsion Formation in Systems with Low Interfacial Tension: Occurence, Properties, and Behavior of Microemulsions," *Journal of Colloid and Interface Science*, 102(1): 206-226 (Nov., 1984).

Overbeek et al., "Microemulsions," in *Surfactants*, Th. F. Thadros, Ed., Academic Press, London, pp. 111-132 (1984).

Ruckenstein et al., "Stability of Microemulsions," *J. Chem. Soc. Faraday Trans II*, vol. 71; pp. 1690-1707 (1975).

Rumphorst, et al. "Examination of the Formulation of an Innovative Single-Component Bonding System," *Signature*, vol. 6, No. 1, pp. 1-3 (Sep. 2000).

Safran et al., "Phase Diagrams for Microemulsions," *Physical Review Letters*, vol. 50, No. 24, pp. 1930-1933 (Jun. 13, 1983).

Xu et al., *J. Phys. Chem.*, 97:11350-11353 (1993).

U.S. Appl. No. 10/847,781, filed May 17, 2004, entitled "Dental Compositions Containing Nanofillers and Related Methods".

U.S. Appl. No. 10/847,782, filed May 17, 2004, entitled "Dental Compositions Containing Nanozirconia Fillers".

U.S. Appl. No. 10/847,803, filed May 17, 2004, entitled "Use of Nanoparticles to Adjust Refractive Index of Dental Compositions" (3M Ref. 59611US002).

U.S. Appl. No. 10/865,649, filed Jun. 10, 2004, entitled "Orthodontic Brace With Polymeric Arch Member".

U.S. Appl. No. 10/916,168, filed Aug. 11, 2004, entitled "Self-etching Dental Compositions and Methods".

U.S. Appl. No. 10/916,169, filed Aug. 11, 2004, entitled "Self-etching Emulsion Dental Compositions and Methods".

U.S. Appl. No. 10/729,497, filed Dec. 5, 2003, entitled "Compositions Including Polymerizable Bisphosphonic Acids and Methods".

U.S. Appl. No. 60/586,326, filed Jul. 8, 2004, entitled "Dental Methods, Compositions, and Kits Including Acid-sensitive Dyes".

U.S. Appl. No. 60/600,658, filed Aug. 11, 2004, entitled "Self-adhesive Compositions Including a Plurality of Acidic Compounds".

U.S. Appl. No. 60/600,558, filed Aug. 11, 2004 entitled Dental Methods, Compositions, and Kits Including Acid-sensitive Dyes.

Dyba, M. et al.; "1-Hydroxyalkane-1,1-diyldiphosphonates as potent chelating agents for metal ions. Potentiometric and spectroscopic studies of copper(II) coordination"; J. Chem Soc., Dalton Trans. 1996; pp. 1119-1123.

Gumienna-Kontecka, E. et al.; "Bisphosphonate chelating agents Coordination ability of 1-phenyl-1-hydroxymethylene bisphosphonate towards $Cu^{2+}$ ions"; Journal of Inorganic Biochemistry 89 (2002) pp. 13-17.

Kieczykowski, G. et al.; "Preparation of (4-Amino-1-Hydroxybutylidene)bisphosphonic Acid Sodium Salt, MK-217 (Alendronate Sodium). An Improved Procedure for the Preparation of 1-Hydroxy-1,1-bisphosphonic Acids"; J. Org. Chem. 1995, 60, pp. 8310-8312.

Mathis, R. et al.; "Properties of a glass-ionomer/resin-composite hybrid material"; Dental Materials, vol. 5, No. 5 Sep. 1989; pp. 355-358.

Abstract No. 51; Journal of Dental Research; vol. 66; 1987; p. 113.

Moszner, N. et al.; "Monomers for adhesive polymers, $2^a$—Synthesis and radical polymerization of hydrolytically stable acrylic phosphonic acids"; Macromol. Chem. Phys., 200, (1999) pp. 1062-1067.

3M Brochure entitled 3M ESPE Adper™ Prompt™ L-Pop™ and Adper™ Prompt™ Self-Etch Adhesives—Technical Product Profile; Title page, Table of Contents and pp. 3, 5-23 and Publication pg.; 3M IPC (2002).

Tromelin, A. et al.; "α Cetophosphonates Et Esters Cycliques D'Hydroxymethylenes Diphosphonates Syntheses, Structures Et Hydrolyse"; Phosphorus and Sulfur, 1986, vol. 27, pp. 301-312.

Tyrian SPE Universal Self-Priming Etchant, Tyrian SPE Gerneral Informatio, Bisco, Inc. Schaumburg, IL [retrieved from the internet on Jul. 7, 2004]<URLhttp://www.bisco.com/instructions/tyrianspe__instr__print.asp> 8 pages.

\* cited by examiner

SELF-ADHESIVE DENTAL COMPOSITIONS AND METHODS

This application claims the benefit of U.S. Provisional Application No. 60/494,603, filed Aug. 12, 2003, which is incorporated herein by reference in its entirety.

BACKGROUND

The restoration of dental structures including caries, decayed dentin or decayed enamel, is often accomplished by the sequential application of a dental adhesive and then a dental material (e.g., a restorative material) to the relevant dental structures. Similarly, adhesives are also used in the bonding of dental materials (e.g., orthodontic appliances, generally utilizing an orthodontic adhesive) to a dental structure. Often various pretreatment processes are used to promote the bonding of dental adhesives to dentin or enamel. Typically, such pretreatment steps include etching, for example, using inorganic or organic acids, followed by priming to improve the bonding between the tooth structure and the overlying adhesive.

Whether for application of dental restoratives (e.g., cured or uncured composites such as glass ionomer cements, modified glass ionomer cements, etc.; fillings; sealants; inlays; onlays; crowns; bridges; etc.) or orthodontic appliances to a dental structure surface, the etchants, primers, and adhesives are typically applied in a step-wise fashion. Often between such steps, one or more rinsing and drying steps are used. As a result, dental restoration and the application of orthodontic appliances typically involve multi-step procedures.

To simplify conventional restorative and/or orthodontic procedures, for example, it would be desirable to provide a single composition that accomplishes both etching and priming. Thus, there is a need for a self-etching primer, particularly a self-etching dental primer, for improved bonding of an adhesive (e.g., a dental adhesive) to a substrate surface (e.g., dental structure, such as dentin, enamel, bone, or other hard tissue) and that could eliminate the conventional post-etching rinsing and drying steps. Furthermore, there is still a need for new compositions that can serve as self-etching adhesives, i.e., adhesive compositions with priming and etching properties that can be applied in a single pretreatment step. In yet other dental and orthodontic procedures, there is a need for restorative compositions (e.g., filling materials and orthodontic adhesives) that can serve as self-adhesive compositions (preferably i.e., one-part, shelf-stable compositions) that can bond to an untreated dental structure (i.e., a structure not pre-treated with an etchant, primer, or bonding agent). Preferred embodiments of the present invention meet some of these needs.

SUMMARY OF THE INVENTION

Current dental adhesives are typically applied with the following steps: 1) the tooth is etched by an acid; 2) the tooth is primed by a primer material; and 3) the adhesive is applied and cured. Suppliers have more recently provided materials in which they have attempted to incorporate two of the steps together in a single step. Some suppliers have provided materials that combine all three steps into one. However in some cases, the dental practitioner is required to premix components before use. In one embodiment of the present invention, a single-step adhesion process is disclosed that allows all three steps to be combined into a single step without requiring the dental practitioner to premix adhesive components.

One approach to providing such a one-step adhesive (i.e., etching, priming, and adhering in one step), is to provide an adhesive that has 1) an acidic component, 2) a formulation able to effectively wet the dental structure, 3) an ionizing liquid (i.e., a liquid that promotes ionizing of acidic components), typically water, and 4) polymerizable compounds (typically (meth)acrylates) that are able to adhere to the dental surface. However, the difficulty in combining water, acidic materials, and methacrylate materials is well documented, since water/acid ionization in the presence of a methacrylate material can typically result in hydrolytic cleavage of the methacrylate. The acidic components, water, and methacrylate components have traditionally been separated into at least two separate containers to avoid hydrolytic cleavage. Combining the separated components requires extensive mixing at specific ratios to work effectively. When the materials are not separated into multiple packages/bottles, the materials generally do not have sufficient shelf-life stability to provide adequate bond strength performance over the projected lifetime of the dental adhesive.

In one aspect, the present invention provides a method of restoring a dental structure. Surfaces (e.g., cut or uncut) of such dental structures include, for example, enamel, dentin, and cementum. Exemplary dental materials include, for example, dental restoratives, orthodontic adhesives, and orthodontic appliances (e.g., including orthodontic appliances precoated with a cured or uncured orthodontic adhesive).

The method includes: applying a non-aqueous, self-adhesive composition to a wet, unetched dental structure surface; and hardening the non-aqueous, self-adhesive composition under conditions effective to form a bond of preferably at least 7 MPa, between the hardened composition and the dental structure. In some embodiments, the method further includes applying an aqueous diluent to the unetched dental structure surface to provide the wet, unetched dental structure surface. Typically, the non-aqueous, self-adhesive composition includes an ethylenically unsaturated compound with acid functionality, an ethylenically unsaturated compound without acid functionality, a filler, and an initiator system. Optionally, the non-aqueous self-adhesive composition includes at least 40% by weight filler.

In another aspect, the present invention provides a dental composition including: an ethylenically unsaturated compound with acid functionality; an ethylenically unsaturated compound without acid functionality; an initiator system; a nonionic surfactant (e.g., a polymerizable surfactant); and a filler; wherein the dental composition is self-adhesive and non-aqueous. In some embodiments, the composition includes at least 40% by weight filler. In some embodiments, the composition is an orthodontic adhesive that can optionally be provided as a precoated orthodontic appliance.

In another aspect, the present invention provides methods of adhering an orthodontic appliance to a tooth. Exemplary orthodontic appliances include brackets, buccal tubes, bands, cleats, buttons, lingual retainers, lingual bars, bite blockers, crowns used for connection to a Herbst appliance, attachment devices for use with tooth positioners, attachment devices for use with removable appliances, and combinations thereof.

In one embodiment, the method includes: applying a non-aqueous, self-adhesive composition to a wet tooth surface under conditions effective to cause the self-adhesive composition to etch the tooth surface; applying an orthodontic appliance to the tooth surface having the self-adhesive composition applied thereon; and hardening the self-adhesive composition under conditions effective to form a bond between the orthodontic appliance and the tooth, wherein the non-aqueous, self-adhesive composition includes: an ethylenically unsaturated compound with acid functionality; an ethylenically unsaturated compound without acid functionality; an initiator system; and at least 40% by weight filler. Optionally, the self-adhesive composition further includes a surfactant.

In another embodiment, the method includes: applying an orthodontic appliance having a non-aqueous, self-adhesive composition thereon to a wet tooth surface under conditions effective to cause the self-adhesive composition to etch the tooth surface; and hardening the self-adhesive composition under conditions effective to form a bond between the orthodontic appliance and the tooth, wherein the non-aqueous, self-adhesive composition includes: an ethylenically unsaturated compound with acid functionality; an ethylenically unsaturated compound without acid functionality; an initiator system; and at least 40% by weight filler. Optionally, the self-adhesive composition further includes a surfactant. In some embodiments, the method further includes applying a non-aqueous, self-adhesive composition to an orthodontic appliance to provide the orthodontic appliance having the non-aqueous, self-adhesive composition thereon. Alternatively, the orthodontic appliance having the non-aqueous, self-adhesive composition thereon can be provided as a pre-coated orthodontic appliance.

Definitions

As used herein, "adhesive" or "dental adhesive" refers to a composition used as a pre-treatment on a dental structure (e.g., a tooth) to adhere a "dental material" (e.g., "restorative," an orthodontic appliance (e.g., bracket), or an "orthodontic adhesive") to the dental structure. An "orthodontic adhesive" refers to a highly (generally greater than 40% by weight) filled composition (more analogous to a "restorative material" than to a "dental adhesive") used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, a "non-aqueous" composition (e.g., an adhesive) refers to a composition in which water has not been added as a component. However, there may be adventitious water in other components of the composition, but the total amount of water does not adversely affect stability (e.g., the shelf-life) of the non-aqueous composition. Non-aqueous compositions preferably include less than 1% by weight, more preferably less than 0.5% by weight, and most preferably less than 0.1% by weight water, based on the total weight of the non-aqueous composition.

As used herein, "substantially free" of organic solvents means that the composition includes less than 10% (preferably less than 5%, more preferably less than 1%) by weight organic solvent. As used herein, an organic solvent refers to an organic compound capable of solubilizing (dissolving, making miscible, etc.) other components in the composition. Commonly used organic solvents typically have a molecular weight less than 100 grams/mole.

As used herein, a "self-etching" composition refers to a composition that bonds to a dental structure surface without pretreating the dental structure surface with an etchant. Preferably, a self-etching composition can also function as a self-primer wherein no separate etchant or primer are used.

As used herein, a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

As used herein, "hardening" or "curing" a composition are used interchangeably and refer to polymerization and/or crosslinking reactions including, for example, photopolymerization reactions and chemical polymerization techniques (e.g., ionic reactions or chemical reactions forming radicals effective to polymerize ethylenically unsaturated compounds) involving one or more materials included in the composition.

As used herein, a "dental structure surface" refers to tooth structures (e.g., enamel, dentin, and cementum) and bone.

As used herein, an "uncut" dental structure surface refers to a dental structure surface that has not been prepared by cutting, grinding, drilling, etc.

As used herein, an "untreated" dental structure surface refers to a tooth or bone surface that has not been treated with an etchant, primer, or bonding agent prior to application of a self-etching adhesive or a self-adhesive composition of the present invention.

As used herein, an "unetched" dental structure surface refers to a tooth or bone surface that has not been treated with an etchant prior to application of a self-etching adhesive or a self-adhesive composition of the present invention.

As used herein, an "etchant" refers to an acidic composition that is capable of fully or partially solubilizing (i.e., etching) a dental structure surface. The etching effect can be visible to the naked human eye and/or instrumentally detectably (e.g., by light microscopy). Typically, an etchant is applied to the dental structure surface for a period of about 10 to 30 seconds.

As used herein, a "wet" dental structure surface refers to a surface of a dental structure upon which an aqueous liquid (e.g., water or saliva) is present and visible to the naked human eye.

As used herein, a "dry" dental structure surface refers to a surface of a dental structure that has been dried (e.g., air dried) and does not have present visible water.

As used herein, "dental material" refers to a material that may be bonded to a dental structure surface and includes, for example, dental restoratives, orthodontic appliances, and/or orthodontic adhesives.

As used herein, an "oil-in-water" emulsion refers to an oil-in-water mixture in which the water forms a continuous phase and the oil is in discontinuous droplets.

As used herein, a "water-in-oil" emulsion refers to a water-in-oil mixture in which the oil forms a continuous phase and the water is in discontinuous droplets. A water-in-oil emulsion can be distinguished from an oil-in-water emulsion by using an electrical emulsion tester according to the method described in the Examples Section. An oil-in-water emulsion will conduct electricity with relatively low resistance since water forms its external or continuous phase, whereas a water-in-oil emulsion will not conduct, or very poorly conduct, electricity.

As used herein, "oil phase" in a water-in-oil emulsion refers to all components in the formulation that individually exceed their solubility limit in the water phase; these are materials that generally have solubilities of less than 1% in distilled water, however, water phase components such as salts may decrease the solubility of certain oils resulting in their partitioning into the oil phase.

As used herein, "water phase" in a water-in-oil emulsion refers to the water present and any components that are water soluble, i.e., have not exceeded their solubility limit in water.

As used herein, a "physically stable" emulsion refers to an emulsion that has no visible water separation following one (preferably, two, and more preferably, three) freeze/thaw/centrifuging cycles according to the Emulsion Stability Test Protocol as described in the Examples Section.

As used herein, a "chemically stable" composition refers to a composition that has a shelf-life of at least one year, and preferably at least 2 years, at room temperature. Shelf-life of a self-adhesive composition is typically measured by determining if the aged composition provides acceptable bond strengths when the aged composition is bonded to a dental structure surface.

As used herein, a "surfactant" refers to a surface-active agent that modifies the nature of a surface (e.g., reduces the surface tension) and encompasses surface-active agents typically referred to as "wetting agents."

As used herein, "(meth)acryl" is a shorthand term referring to "acryl" and/or "methacryl." For example, a "(meth)acryloxy" group is a shorthand term referring to either an acryloxy group (i.e., $CH_2=CHC(O)O-$) and/or a methacryloxy group (i.e., $CH_2=C(CH_3)C(O)O-$).

As used herein, "a" or "an" means "at least one" or "one or more" unless otherwise indicated.

DETAILED DESCRIPTION OF ILLUSTRATIVE EMBODIMENTS

Compositions of the present invention are useful for treating hard surfaces, preferably, hard tissues such as dentin, enamel, and bone. Compositions of the present invention are particularly desirable to etch, preferably etch and prime, at least one type of dental structure (e.g., dentin, enamel, or bone). The compositions of the present invention can be used with an overlying adhesive (e.g., a dental adhesive), but they more preferably can be used as the adhesive (i.e., a self-etching adhesive). In some embodiments, compositions of the present invention may also be useful as the overlying adhesive. In some other embodiments, compositions of the present invention can be used as a restorative material (e.g., filling material) without the need for an etchant, primer, or adhesive.

A composition that etches and primes a surface in one step could eliminate conventional post-etching rinsing and drying steps. An adhesive can then be applied over the etched and primed surface. In certain preferred embodiments, the compositions are self-etching adhesives. That is, they etch, and typically prime, a surface in one step and function as an adhesive.

Such self-etching primer and self-etching adhesive compositions are typically prepared by combining polymerizable components (e.g., ethylenically unsaturated compounds with acid functionality and ethylenically unsaturated compounds without acid functionality) and an initiator system. See, for example, U.S. application Ser. No. 10/916,168, filed on Aug. 11, 2004, entitled "SELF-ETCHING DENTAL COMPOSITIONS AND METHODS"; and U.S. application Ser. No. 10/916,169, filed on Aug. 11, 2004, entitled "SELF-ETCHING EMULSION DENTAL COMPOSITIONS AND METHODS". Typically, the selection of polymerizable components is made to impart the desired etching, priming, adhesive, and/or restorative properties to the compositions. Generally, techniques for selecting polymerizable components and optional other components to impart etching, priming, adhesive, and/or restorative properties to hard-surface treatment compositions are well known to those skilled in formulation of dental materials. Suitable polymerizable components for use in such compositions, dental adhesives, and dental restoratives are discussed herein.

Compositions of the present invention can be used to promote the adhesion of dental materials to dental structures. Exemplary dental materials include, but are not limited to, dental restoratives, orthodontic appliances, and orthodontic adhesives. Compositions of the present invention can be the dental restorative or the orthodontic adhesive. Dental restoratives include, for example, composites, fillings, sealants, inlays, onlays, crowns, and bridges. Orthodontic appliances include, for example, brackets; buccal tubes; bands; cleats; buttons; lingual retainers; lingual bars; bite blockers; crowns used for connection to a Herbst appliance; attachment devices for use with tooth positioners and other removable appliances such as those described, for example, in U.S. Pat. No. 6,309,215 (Miller et al.) and pending U.S. patent application Ser. No. 10/865,649 filed Jun. 10, 2004 (Cinader et al.); and other devices capable of changing or retaining tooth position. Orthodontic appliances can optionally be precoated with an orthodontic adhesive. Orthodontic adhesives can be uncured or cured (e.g., as encountered in indirect bonding methods).

In some embodiments, the compositions are hardened (e.g., polymerized by conventional photopolymerization and/or chemical polymerization techniques) prior to applying the dental material. In other embodiments, the compositions are hardened (e.g., polymerized by conventional photopolymerization and/or chemical polymerization techniques) after applying the dental material. It is significant if the composition can be formulated to promote adhesion to both enamel and dentin. It is particularly significant if the composition can be formulated to function as the etchant, primer, and adhesive to both enamel and dentin. It is also particularly significant if the composition can be formulated to function as the etchant, primer, adhesive, and restorative material (or orthodontic adhesive) for both enamel and dentin.

Suitable photopolymerizable compositions that can be used as dental materials and dental adhesive compositions in methods of the present invention can include epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional (meth)acrylates.

Compositions of the present invention can optionally include fillers, surfactants, solvents, and other additives. Various combinations of the components described herein can be used in the compositions of the present invention.

Certain preferred non-aqueous compositions (preferably, adhesives) (i.e., including less than 1% by weight water in the composition) of the present invention have enhanced chemical stability. That is, they have, for example, a room-temperature shelf-life stability of at least 1 year, and preferably at least 2 years. Additionally, such non-aqueous compositions (preferably, adhesives) may be applied directly to a wet dental structure surface (preferably a tooth surface). Alternatively, preferred non-aqueous compositions (preferably, adhesives) may be mixed (e.g., on a brush tip) with a diluent (e.g., water or water in combination with a surfactant) prior to applying to a wet or dry dental structure surface (preferably a tooth surface).

Certain preferred aqueous-based compositions (preferably, adhesives) (i.e., including water in the composition) of the present invention are water-in-oil based emulsions, preferably micro-emulsions. Preferably, the water-in-oil based emulsions have suitable chemical (preferably, hydrolytic) stability. That is, they have, for example, a room-temperature shelf-life stability of at least 1 year, and preferably at least 2 years. Additionally, preferred compositions do not require any pre-mixing steps prior to application to the surface of the dental structure.

Certain preferred water-in-oil emulsions are also physically stable. That is, there is no visible water separation in the emulsion following one (preferably, two, and more preferably, three) freeze/thaw/centrifuging cycles according to the Emulsion Stability Test Protocol as described in the Examples Section.

Ethylenically Unsaturated Compounds with Acid Functionality

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates.

Ethylenically unsaturated compounds with acid functionality include, for example, $\alpha,\beta$-unsaturated acidic compounds such as glycerol phosphate mono(meth)acrylates, glycerol phosphate di(meth)acrylates, hydroxyethyl (meth) acrylate (e.g., HEMA) phosphates, bis((meth)acryloxyethyl) phosphate, ((meth)acryloxypropyl) phosphate, bis((meth) acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth) acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable resin system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA: IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Provisional Application Ser. No. 60/600,658, filed Aug. 11, 2004, entitled "SELF-ADHESIVE COMPOSITIONS INCLUDING A PLURALITY OF ACIDIC COMPOUNDS".

Preferably, the compositions of the present invention include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Ethylenically Unsaturated Compounds without Acid Functionality

The compositions of the present invention also include one or more polymerizable components in addition to the ethylenically unsaturated compounds with acid functionality, thereby forming hardenable compositions. The polymerizable components may be monomers, oligomers, or polymers.

In certain embodiments, the compositions are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Preferably, compositions of the present invention include at least 5% by weight, more preferably at least 10% by weight, and most preferably at least 15% by weight ethylenically unsaturated compounds without acid functionality, based on the total weight of the unfilled composition. Preferably, compositions of the present invention include at most 95% by weight, more preferably at most 90% by weight, and most preferably at most 80% by weight ethylenically unsaturated compounds without acid functionality, based on the total weight of the unfilled composition.

Photopolymerizable Compositions

Suitable photopolymerizable compositions may include photopolymerizable components (e.g., compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[l-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl(meth)acrylate; glycerol mono- or di-(meth) acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis [4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

Preferred photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. Publication No. 2003/0166737 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Chemically Polymerizable Compositions

The chemically polymerizable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Preferably, the reducing agent is present in an amount of at least 0.01% by weight, and more preferably at least 0.1% by weight, based on the total weight (including water) of the components of the polymerizable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

Surfactants

Surfactants useful in compositions and methods of the present invention include, for example, nonionic surfactants, cationic surfactants, anionic surfactants, and combinations thereof. Surfactants useful in compositions and methods of the present invention include non-polymerizable and polymerizable surfactants.

Non-polymerizable nonionic surfactants are well known to those of skill in the art. Exemplary non-polymerizable nonionic surfactants include, for example, polyoxyethylene alcohols (BRIJ series), polyoxyethylene acids (MYRJ series), polyoxyethylene fatty acids (TWEEN series), sorbitan fatty acid esters (SPAN series), alcohol ethoxylates (RHODASURF series), nonyl phenolaromatic ethoxylates (IGEPAL series), and the like.

Useful polymerizable nonionic surfactants typically have polymerizable groups such as ethylenically unsaturated groups, for example, styryl and allyl groups, as well as (meth)acrylate compounds such as hydroxyethyl methacrylate, hydroxypropyl methacrylate, glycerol dimethacrylate, pentaerythritol triacrylate, and the like, that are attached (e.g., via a urethane linkage) to a hydrocarbon group (e.g., hexyl, cyclohexyl, pentyl, or octyl) or a polyethylenegycol chain. The methacrylate or acrylate moiety (hereafter written as (meth)acrylate) together with the hydrocarbon group moiety form a nonpolar hydrophobic end, while the polyethylene glycol chain forms a polar hydrophilic end. By varying the number of (meth)acrylate groups and the length or number of the polyethylene glycol or chains, surfactants with a wide variety of properties may be produced. In addition to the (meth)acrylate groups, other non polar groups such as fatty acids may also be incorporated to provide an even more hydrophobic end as desired. The polyethylene glycol chain may further be broken into several short chains if desired.

Useful polymerizable nonionic surfactants are well known to those of skill in the art and include, for example, the polymerizable nonionic surfactants available under the trade designations NOIGEN RN-10, NOIGEN RN-20, and NOIGEN RN-50, from DAI-Ichi Kogyo Seiyaku Co. Ltd., Japan (William H. Minkema, MINK Inc., Plymouth, Minn.). Other suitable polymerizable nonionic surfactants include, for example, those disclosed in U.S. Pat. No. 6,387,982 (Blackwell).

Polymerizable anionic surfactants are well known to those of skill in the art and include, for example, those disclosed in U.S. Pat. No. 4,814,514 (Yokota et al.), U.S. Pat. No. 4,939, 283 (Yokota et al.), U.S. Pat. No. 5,324,862 (Yokota et al.), and U.S. Pat. No. 5,332,854 (Yokota et al.).

For embodiments of the present invention where the compositions include a surfactant, the compositions preferably include at least 0.1% by weight, more preferably at least 0.3% by weight, and most preferably at least 0.4% by weight surfactant, based on the total weight of the unfilled composition. For such embodiments, the compositions preferably include at most 50% by weight, more preferably at most 30% by weight, and most preferably at most 15% by weight surfactant, based on the total weight of the unfilled composition.

For embodiments of the present invention where a diluent includes a surfactant, the diluent preferably includes at least 0.1% by weight, more preferably at least 0.3% by weight, and most preferably at least 0.4% by weight surfactant, based on the total weight of the diluent. For such embodiments, the diluent preferably includes at most 50% by weight, more preferably at most 30% by weight, and most preferably at most 15% by weight surfactant, based on the total weight of the diluent.

Fillers

The compositions of the present invention can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 0.1 micrometers, and more preferably less than 0.075 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially preferred in certain embodiments.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Other suitable fillers are disclosed in U.S. Pat. No. 6,387, 981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. patent application Ser. Nos. 10/847,781; 10/847,782; and 10/847,803; all three of which were filed on May 17, 2004.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., wherein the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition.

Optional Photobleachable Dye

In some embodiments, compositions of the present invention preferably have an initial color remarkably different than dental structures. Color is preferably imparted to the composition through the use of a photobleachable dye. The composition preferably includes at least 0.001% by weight photobleachable dye, and more preferably at least 0.002% by weight photobleachable dye, based on the total weight of the composition. The composition preferably includes at most 1% by weight photobleachable dye, and more preferably at most 0.1% by weight photobleachable dye, based on the total weight of the composition. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 20; more preferably, $\Delta E^*$ is at least 30; most preferably $\Delta E^*$ is at least 40.

Optional Additives

Optionally, compositions of the present invention may contain solvents (e.g., alcohols (e.g., propanol, ethanol), ketones (e.g., acetone, methyl ethyl ketone), esters (e.g., ethyl acetate), and other nonaqueous solvents (e.g., dimethylformamide, dimethylacetamide, dimethylsulfoxide, 1-methyl-2-pyrrolidinone)).

If desired, the compositions of the invention can contain additives such as indicators, dyes, pigments, inhibitors, accelerators, viscosity modifiers, wetting agents, tartaric acid, chelating agents, buffering agents, stabilizers, and other similar ingredients that will be apparent to those skilled in the art. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Diluents

In some specific embodiments of the present invention, an aqueous diluent (i.e., a diluent including water) is applied to a dental structure surface to wet the surface. In some specific embodiments of the present invention, non-aqueous compositions (preferably, adhesive compositions) are mixed with a diluent for application to a dental structure surface (preferably a tooth surface).

In some embodiments, the aqueous diluent consists essentially of water or water in combination with a surfactant. The water can be distilled, deionized, or plain tap water. Generally, deionized water is preferred. Suitable surfactants are described herein above.

In some embodiments, the aqueous diluent can include, for example, an acid sensitive dye, an antibacterial agent, a water soluble monomer, a pH adjuster agent, a buffer, a stabilizer, a surfactant, a fluoride anion, a fluoride releasing agent, or combinations thereof. Suitable acid-sensitive dyes include, for example, those disclosed in U.S. Provisional application No. 60/600,558, filed Aug. 11, 2004, entitled "DENTAL METHODS, COMPOSITIONS, AND KITS INCLUDING ACID-SENSITIVE DYES", and U.S. Provisional application No. 60/586,326, entitled "DENTAL METHODS, COMPOSITIONS, AND KITS INCLUDING ACID-SENSITIVE DYES", filed Jul. 8, 2004.

For embodiments in which the aqueous diluent is mixed with non-aqueous compositions of the present invention, the amount of diluent should be sufficient to provide adequate handling and mixing properties and to permit the transport of ions, particularly in the filler-acid reaction. Preferably, water represents at least 2% by weight, and more preferably at least 5% by weight, of the total weight of ingredients used to form the composition. Preferably, water represents no greater than 90% by weight, and more preferably no greater than 80% by weight, of the total weight of ingredients used to form the composition.

Water-In-Oil Emulsions

Certain preferred aqueous-based compositions of the present invention are water-in-oil based emulsions, preferably micro-emulsions.

The emulsions preferably include at least 1% by weight water, more preferably, at least 3% by weight water, and most preferably, for certain embodiments, the emulsions include at least 5% by weight water, based on the total weight of the emulsion. They preferably include no more than 70% by weight water, and more preferably, no more than 50% by weight water, based on the total weight of the emulsion.

Typically emulsifiers and/or surfactants are used in the preparation of the emulsions of the present invention. The addition of low levels of stabilizing ingredients in the water phase can also be advantageous. Salts such as magnesium sulfate may be useful emulsion stabilizers. The addition of water-soluble gums such as guar derivatives, xanthan gum, and thickeners such as hydroxy ethyl cellulose, hydroxy propyl cellulose and carboxyl vinyl polymers may be helpful in stabilizing the emulsion.

A typical method for preparing water-in-oil macroemulsions includes heating, independently, the oil phase (containing the polymer and optional ingredients, e.g., surfactants) and the water phase (containing optional ingredients, e.g., surfactants and/or stabilizing ingredients), and slowly adding the water phase to the oil phase with good agitation. Homogenization is preferred, but may not be necessary. Upon cooling, other optional ingredients may be added, e.g., fillers. For the preparation of other water-in-oil macroemulsions, heating may not be necessary. Often the successful preparation of a macroemulsion depends on factors such as temperature, mixing rates and times, shear forces, etc.

In other embodiments, a water-in oil emulsion can be prepared by first mixing the relatively polar components of the composition (e.g., a phosphoric acid ester monomer, polar solvents, surfactant, and water) to provide the emulsion followed by the addition of the relatively nonpolar components of the composition.

Another method that can be used to prepare water-in oil emulsions that are useful as self-etching adhesive compositions, is to prepare an inverse micelle system involving water droplets of micron or submicron size encapsulated by an appropriate surfactant as described, for example, in the present examples (e.g., see Example 46). For a discussion of inverse micelles and the general solubilization of organic compounds, see, for example, Xu et al., *J. Phys. Chem.,* 97:11350-11353 (1993); and Baneijee et al., *Ind. Eng. Chem. Res.,* 35:3100-3107 (1996).

Microemulsions can be oil-in-water (O/I) or water-in-oil (W/O) type, but the latter type is of particular interest in the present invention. Water-in-oil type microemulsions are formed under the conditions of dispersing water droplets having a size of at most 100 nanometers, typically obtained by the adsorption of a surfactant and a co-surfactant at the water/oil interface to lower the interfacial surface tension. The theory of microemulsions is available in the scientific literature including, for example, Leung et al, Chapter 9 in "Surfactants in Chemical Process Engineering," Marcel Dekker (1988); Overbeek et al., "Surfactants" in *Microemulsions*, Academic Press (1984); Safran et al., *Phys. Rev. Lett.,* 50:1930 (1983); Ruckenstein et al., *J. Chem. Soc. Faraday Trans,* 2, 71:1690 (1975); and Ostrovsky et al., *J. Colloid. Interface Sci.,* 102:206 (1984); and Chapter 6 of "Microemulsions", pp. 138-155 (Holmberg et al.) in *Surfactants and Polymers in Aqueous Solution*; Second Edition, John Wiley & Sons, (2003; Reprinted with corrections in 2004).

In a typical procedure for making a water-in-oil microemulsion, the water is added slowly with mixing as a final step to the remaining components of the composition until initial turbidity is achieved. Often during this "titration" procedure the microemulsion forms spontaneously at the point of initial turbidity. This generally requires from 8 weight % to 12 weight % water based on the total weight of the composition. Typically, the microemulsion is formed by simple mixing and the oil and water-components of the composition do not need to be pre-mixed separately or heated prior to the addition of the water.

Methods of Use

Exemplary methods of using compositions of the present invention are described in the Examples. In some embodiments of the present invention, conditions effective to cause a composition (preferably adhesive) to etch a dental structure surface include swishing the adhesive and/or adhesive/diluent mixture with a brush to mix/rubbing dental structure surface for a time effective to etch (i.e., for at least 3 seconds), typically for at least 5 seconds, often times for at least 10 seconds, and sometimes for at least 20 seconds.

In order to achieve effective etching activity on a dental structure surface, it is generally important that water be present at the time of treatment. This objective of having water present can be achieved by a variety of techniques and methods as exemplified in the Examples Section. Briefly, several typical methods are listed:

A first method is for the practitioner to leave the structure surface wet with water after rinsing, and therefore, eliminate or partially eliminate a typical drying step before structure treatment. A non-aqueous, self-etching dental composition (e.g., a self-etching adhesive, a self-adhesive composition, or an orthodontic adhesive) can than be applied to the structure surface and cured using conventional methods.

A second method ("wet-brush" technique) is to sequentially dip a dental applicator into an aqueous diluent (e.g. water or water plus one or more additives), and then mix the wet brush with a non-aqueous, self-etching dental composition (e.g., a self-etching adhesive). The resulting aqueous mixture can than be applied to the structure surface and cured using conventional methods.

A third method is to sequentially treat a dry dental structure surface with an aqueous diluent (e.g. water or water plus one or more additives), followed by the application of a non-aqueous, self-etching dental composition (e.g., a self-etching adhesive, a self-adhesive composition, or an orthodontic adhesive). The resulting treated surface can then be further treated and cured using conventional methods.

In the case of aqueous, self-etching compositions (e.g., a self-etching, water-in-oil emulsion adhesive), the composition can be applied to a dry dental structure surface using conventional techniques. Typically, such a self-etching, water-in-oil emulsion adhesive is applied to a structure surface for about 20 seconds with an applicator brush, air-dried under gentle air flow for 20-25 seconds, and light-cured for about 10 seconds. Finally a dental material (e.g., a dental restorative) can be applied to the cured adhesive layer and light-cured for about 20 seconds.

Methods of bonding a dental material to a dental structure surface preferably result in a bond to enamel or dentin (or preferably both), of at least 7 MPa, more preferably at least 15, MPa, and most preferably at least 20 MPa.

The present invention is illustrated by the following examples. It is to be understood that the particular examples, materials, amounts, and procedures are to be interpreted broadly in accordance with the scope and spirit of the invention as set forth herein. Unless otherwise indicated, all parts and percentages are on a weight basis, all water is deionized water, and all molecular weights are weight average molecular weight.

EXAMPLES

Test Methods

Adhesion Shear Bond Strength to Enamel or Dentin Test Method

Adhesive shear bond strength to enamel or dentin for a given test sample was evaluated by the following procedure.

Preparation of Teeth. Bovine incisal teeth, free of soft tissue, were embedded in circular acrylic disks. The embedded teeth were stored in water in a refrigerator prior to use. In preparation for adhesive testing, the embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process. The polished teeth were stored in deionized water and used for testing within 2 hours after polishing. The teeth were allowed to warm in a 36° C. oven to between room temperature (23° C.) and 36° C. before use.

Teeth Treatment. An adhesive test sample was applied with a dental applicator brush over the entire surface of the prepared enamel or dentin surface according to the specific application techniques detailed in the Examples. After application, the adhesive coating was light cured for 10 seconds with an XL 3000 dental curing light (3M Company, St. Paul, Minn.). A 2.5-mm thick Teflon mold with a hole approximately 4.7 mm in diameter was clamped to the embedded tooth such that the hole in the mold exposed part of the adhesively prepared tooth surface. A composite material, A2 shade of FILTEK Z250 Universal Restorative (3M Company), was filled into the hole such that the hole was completely filled, but not overfilled, and light cured for 20 seconds to form a "button" that was adhesively attached to the tooth.

Adhesive Bond Strength Testing. The adhesive strength of a cured test example was evaluated by mounting the assembly (described above) in a holder clamped in the jaws of an INSTRON testing machine (Instron 4505, Instron Corp. Canton, Massachusetts) with the polished tooth surface oriented parallel to the direction of pull. A loop of orthodontic wire (0.44-mm diameter) was placed around the Z250 button adjacent to the polished tooth surface. The ends of the orthodontic wire were clamped in the pulling jaw of the INSTRON apparatus and pulled at a crosshead speed of 2 mm/min, thereby placing the adhesive bond in shear stress. The force in kilograms (kg) at which the bond failed was recorded, and this number was converted to a force per unit area (units of kg/cm$^2$ or MPa) using the known surface area of the button. Each reported value of adhesion to enamel or adhesion to dentin represents the average of 4 to 5 replicates.

Emulsion Stability

A 10-milliliter (10-ml) sample of an emulsion formulation was placed in a 15-ml conical-shaped graduated plastic centrifuge tube (Corning), frozen for approximately 2 hours at approximately −20° C., thawed to room temperature for approximately 2 hours, and centrifuged at 3,000 revolutions per minute (rpm) for 10 minutes using a Labofuge B, model 2650 manufactured by Heraeus Sepatech GmbH, Osterode, West Germany. This cycle of freezing/thawing/centrifuging was repeated for a total of three times. A stable formulation will have no visible water separation in the bottom of the tube.

Emulsion Conductivity Test

An emulsion sample was tested with an Electrical Emulsion Tester (EET) (EET information available from ICI Americas, Inc. Bridgewater, N.J.) in order to distinguish between a water-in-oil emulsion and an oil-in-water emulsion. An oil-in-water emulsion will conduct electricity since water includes its external or continuous phase, whereas a water-in-oil emulsion (free of conductive agents having solubility in the oil phase) will not conduct electricity. The EET consists of resistor electric contacts (30,000 ohm, 0.5 watt), a resistor neon lamp (56,000 ohm, Type NE-51), and a push-button switch all wired in series. To conduct the test, the electric contacts were placed into a sample of the emulsion and the push-button switch was turned on. The lamp would glow in the case of an oil-in-water emulsion and would not glow in the case of a water-in-oil emulsion (free of conductive agents having solubility in the oil phase).

Curing Test Method

A test sample (0.1 g) of resin or resin plus filler (i.e., filled paste), was dispensed out of a syringe onto a dental mixing pad in form of a bead. The test sample was irradiated with a XL 3000 halogen dental light (3M Company) for 40 seconds. Following irradiation, the sharp edge of a dental stainless steel spatula was used to indent the cured sample with an approximate force of 2 Kgf. The curing was judged "OK" when there was no indentation, "Soft" when the sample was broken into pieces, or "No Setting" when the sample stayed in a liquid or paste state. In Table 1, "YES" includes observations of "OK" and "Soft"; and "NO" is the same as "No Setting".

Storage Stability Test Method

Test samples were stored at 45° C. (ca. 30% relative humidity) and evaluated daily for 3 days and then weekly to determine the storage stability of the samples. A test sample was determined to be stable at a given point in time if the sample remained in a non-hardened form and if a hardened composition was formed when the sample was irradiated with a XL 3000 dental curing light (3M Company) for 40 seconds. The number of days that a test sample remained stable was reported as the average of 2 replicates.

Adhesion to Enamel or Dentin Test Method

Adhesive strength to enamel or dentin for a given test sample was evaluated by the following procedure.

Preparation of Teeth. For each test sample, five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 600 silicon carbide paper-backed abrasive on the lapidary wheel. The polished teeth were stored in deionized water and used for testing within 2 hours after polishing. The polished teeth were removed from the water and blotted dry such that the tooth surface had visible water on up to 50% of the total surface at the time of adhesive application.

Teeth Treatment. Previously made molds of 2-mm thick TEFLON sheeting with a 5-mm diameter hole punched through the sheeting were filled with Z100 composite samples (3M Company). The Z100 composite samples were exposed to radiation from a XL 3000 dental curing light for 60 seconds. The resulting hardened Z100 test buttons were removed from the molds and one side of each button was roughened with 320-grit sandpaper. In a controlled environment of 24° C. and 50% relative humidity and within one minute of preparing a test sample, a layer of the test sample was applied with a spatula to the roughened side of the Z100 button. The button with the applied test sample facing the tooth was pressed onto the tooth surface to create an assembly. The assembly was allowed to stand for an additional minute. Thereafter, the test sample layer was exposed to a XL 3000 dental curing light (3M Company) for 40 seconds. The entire assembly was placed in a humidity chamber set at 97% relative humidity and 37° C. for 15 minutes. The assembly was then placed into 37° C. deionized water for 24 hours.

Adhesive Bond Strength Testing. The adhesive strength of a cured test example was evaluated by mounting the assembly (described above) in a holder clamped in the jaws of an INSTRON testing machine (Instron 4505, Instron Corp. Canton, Mass.) with the polished tooth surface oriented parallel to the direction of pull. A loop of orthodontic wire (0.44-mm diameter) was placed around the Z100 button adjacent to the polished tooth surface. The ends of the orthodontic wire were clamped in the pulling jaw of the INSTRON apparatus and pulled at a crosshead speed of 2 mm/min, thereby placing the adhesive bond in shear stress. The force in kilograms (kg) at which the bond failed was recorded, and this number was converted to a force per unit area (units of $kg/cm^2$ or MPa) using the known surface area of the button. Each reported value of adhesion to enamel or adhesion to dentin represents the average of 5 replicates.

Compressive Strength (CS) Test Method

Compressive strength was evaluated by first injecting a test sample into a glass tube having a 4-mm inner diameter. The ends of the glass tube were plugged with silicone plugs. The filled tubes were subjected to 0.275 megapascal (MPa) pressure for 5 minutes, irradiated with a XL 1500 curing light (3M Company) for 80 seconds, and placed in a KULZER UniXS (Kulzer, Inc., Germany) light box for 180 seconds. Five such cured samples were cut to a length of 8 mm and placed in 37° C. water for 1 day. Compressive strength was determined according to ISO Standard 7489 using an INSTRON universal tester (Instron Corp., Canton, Mass.) operated at a crosshead speed of 1 millimeter per minute (mm/min). Results were reported as the average of 5 replicates.

Diametral Tensile Strength (DTS) Test Method

Diametral tensile strength was measured using the above-described CS procedure, but using samples were cut to a length of 2 mm. Results were reported as the average of 5 replicates.

TABLE A

Abbreviations, Descriptions, and Sources of Materials

| Abbreviation | Description and Source of Material |
| --- | --- |
| TEGDMA | Triethyleneglycol dimethacrylate (Sartomer, Exton, PA) |
| HEMA | 2-Hydroxyethyl methacrylate (Sigma-Aldrich, St. Louis, MO) |
| NPGDMA | Neopentylglycol dimethacrylate (Sigma-Aldrich) |
| BisGMA | 2,2-Bis[4-(2-hydroxy-3-methacryloyloxy-propoxy)phenyl]propane; CAS No. 1565-94-2 |
| UDMA | Diurethane dimethacrylate (CAS No. 41137-60-4), commercially available as Rohamere 6661-0 (Rohm Tech, Inc., Malden, MA) |
| EGDM | Ethylene glycol dimethacrylate (Sigma-Aldrich) |
| DEGDM | Di(ethylene glycol) dimethacrylate (Sigma-Aldrich) |
| PEG 400 DMA | Polyethyleneglycol dimethacrylate (MW about 570; Sartomer) |
| BisEMA6 | Ethoxylated bisphenol A dimethacrylate (Sartomer) |
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity $\rho$ = 4.64. |
| IEM | 2-Isocyanatoethyl methacrylate (Sigma-Aldrich) |
| VBM | Polymer made by reacting AA:ITA copolymer with sufficient IEM to convert 16 mole percent of the acid groups of the copolymer to pendent methacrylate groups, according to the dry polymer preparation of Example 11 of U.S. Pat. No. 5,130,347. |
| GDMA-P | Glycerol dimethacrylate phosphate . . . Prepared as described in J. Dent. Res., 35, 8466 (1956) . . . cited in EP 0 237 233 (Oxman); (Also, see Example 3 in International Publication WO 02/092021 (Hecht et al.)) |

TABLE A-continued

Abbreviations, Descriptions, and Sources of Materials

| Abbreviation | Description and Source of Material |
| --- | --- |
| MHP-A | Methacryloyloxyhexyl phosphate ($POCl_3$ derived) (See Preparation Method described herein) |
| MHP-B | Methacryloyloxyhexyl phosphate ($P_2O_5$ derived) (See Preparation Method described herein) |
| MDP-A | Methacryloyloxydecyl phosphate ($POCl_3$ derived) (See Preparation Method described herein) |
| MDP-B | Methacryloyloxydecyl phosphate ($P_2O_5$ derived) (See Preparation Method described herein) |
| PM-2 | KAYAMER PM-2; Bis(methacryloxyethyl) phosphate (Nippon Kayaku, Japan) |
| Ebecryl 168 | Bis(methacryloxyethyl) phosphate (UCB SA, Brussels, Belgium) |
| CMA-P | Caprolactone methacrylate phosphate (See Preparation Method described herein) |
| HEMA-P | Mixture of mono-, di-, tri-HEMA phosphate and tetraHEMA pyrophosphate. (See Preparation Method described herein) |
| AcAc MA | 2-(Methacryloyloxy)ethyl acetoacetate (Sigma-Aldrich) |
| $ZrO_2$ Filler | Surface-treated zirconia filler (nano-sized primary particles) (See Preparation Method described herein) |
| RN-50 | NOIGEN RN-50 polymerizable nonionic surfactant (DAI-Ichi Kogyo Seiyaku Co. Ltd., Japan; William H. Minkema, MINK Inc., Plymouth, MN) |
| AOT-100 | Sodium bis(2-ethylhexyl)sulfocuccinate (Sigma-Aldrich) |
| LA 010 | GENAPOL LA 010 (Formerly GENEPOL 26-L-1) C12 to C16 natural linear alcohol ethoxylated with 1 mole of ethylene oxide; CAS No. 68551-12-2 (Clarient Corp, Functional Materials Division, Sulzbacham Taunus, Germany) |
| BHT | Stabilizer; 2,6-Di-tert-butyl-4-methylphenol (Sigma-Aldrich, St. Louis, MO) |
| Zr-Si Filler | Silane-treated zirconia-silica (Zr-Si) filler prepared as described in U.S. Pat. No. 4,503,169 (Randklev) |
| AEROSIL R812S | Fumed silica (Degussa, Germany) |
| $Ca(OH)_2$ | Calcium hydroxide (Sigma-Aldrich) |
| Photac FAS | Fluoroaluminasilicate glass (3M ESPE, Seefeld, Germany) (See Example 3 in International Publication WO 02/092021 (Hecht et al.)) |

TABLE B

Abbreviations, Descriptions, and Sources of Materials

| Abbreviation | Description and Source of Material |
| --- | --- |
| t-BDMA | 4-tert-Butyl dimethylaniline (Sigma-Aldrich) |
| DMAPE | 4-Dimethylaminophenethanol (Sigma-Aldrich) |
| EDMAB | Ethyl 4-(N,N-dimethylamino)benzoate (Sigma-Aldrich) |
| DHEPT | Dihydroxyethyl p-toluidine (Gefachem-Prochemie, Leverkusen, Germany) |
| DMA | N,N-Dimethylaniline (Sigma-Aldrich) |
| DMABN | N,N-Dimethylaminobenzonitrile (Sigma-Aldrich) |
| DMABA | 4-Dimethylaminobenzaldehyde (Sigma-Aldrich) |
| 4-DMAB | 4-Dimethylaminobenzoic acid (Alfa Aesar, Wardhill, MA) |
| 3-DMAB | 3-Dimethylaminobenzoic acid (Lancaster Synthesis Ltd., Windham, NH) |
| 4-DMABn | 4-Dimethylaminobenzoin (Sigma-Aldrich) |
| TEAB | Triethanolaminobenzoate (3M ESPE, Seefeld, Germany) |
| N-PhG | N-phenylglycine (Sigma-Aldrich) |
| N-PhGEE | N-phenylglycine ethyl ester (Eastman Kodak, Rochester, NY) |
| DMAEMA | 2-Dimethylaminoethyl methacrylate (Sigma-Aldrich) |
| TEA | Triethylamine (J. T. Baker, Phillipsburg, NJ) |
| ATU | Allylthiourea (Sigma-Aldrich) |
| DPIPF6 | Diphenyliodonium hexafluorophosphate (Johnson Matthey, Alpha Aesar Division, Ward Hill, NJ) |

TABLE B-continued

Abbreviations, Descriptions, and Sources of Materials

| Abbreviation | Description and Source of Material |
| --- | --- |
| CPQ | Camphorquinone (Sigma-Aldrich) |
| Cu(OAc)$_2$ | Copper (II) Acetate (Sigma-Aldrich) |
| EYB | Erythrosine yellowish blend (Sigma-Aldrich) |
| MOST | 2-(p-Methoxystyryl)-4,6-bis(trichloromethyl)-s-triazine (Described in EP 0 237 233 A2 (Oxman)) |
| IRGACURE 819 | Phosphine oxide photoinitiator (Ciba Specialty Chemicals Corp., Terrytown, NY) |

Starting Materials Preparations

10-Methacryloxydecyl Phosphate (MDP-A from POCl$_3$)

10-Hydroxydecyl Methacrylate Synthesis: A mixture of 1,10-decanediol (206.62 g, 1.19 mol), methacrylic acid (92.40 g, 1.06 mol), p-toluenesulfonic acid hydrate (10.00 g, 53 mmol), and 2,6-di-tert-butyl-4-methylphenol (0.50 g) were heated to 85° C. under aspirator pressure for four hours. The water liberated during the reaction was removed through a distillation head. After cooling to room temperature, hexane (500 mL) was added and the mixture was filtered. The filtrate was then extracted with 1M aqueous NaOH solution (150 mL) followed by saturated salt water (150 mL). The organic phase was then dried over MgSO$_4$ and the solvent was removed under reduced pressure to give a yellow oil (204 g). NMR analysis indicates a mixture of 82 mol % 10-hydroxydecyl methacrylate and 18 mol % 1,10-decane dimethacrylate.

10-Methacryloxydecyl Phosphate (MDP-A) Synthesis: To a mixture of phosphorous oxychloride (POCl$_3$, 69.09 g, 0.45 mol) in dry tetrahydrofuran (400 mL) cooled to −40° C. was added a solution of 10-hydroxydecyl methacrylate (140.00 g, 0.45 mol hydroxyl groups) and triethylamine (45.54 g, 0.45 mol) dropwise over one hour. After full addition, the mixture was stirred at −40° C. for three hours. Water (16.20 g, 0.90 mol) was then added dropwise, and the mixture was stirred for 15 minutes. Triethylamine (91.07 g, 0.90 mol) was then added slowly and the mixture was allowed to warm to room temperature. After stirring at room temperature for 17 hours, the mixture was filtered. Hydroquinone (0.30 g) and 2,6-di-tert-butyl-4-methylphenol (0.25 g) were added to the filtrate. The solvent was then removed under reduced pressure to give a yellow oil (118.02 g). Final product (MDP-A) was characterized by NMR analysis.

10-Methacryloxydecyl Phosphate (MDP-B from P$_2$O$_5$)

10-Methacryloxydecyl phosphate (MDP-B) was prepared as described below for 6-methacryloxyhexyl phosphate (MHP-B from P$_2$O$_5$), except that 1,10-decanediol was substituted for 1,6-hexanediol. Chemical characterization was by NMR analysis.

6-Methacryloxyhexyl Phosphate (MHP-A from POCl$_3$)

6-Methacryloxyhexyl phosphate (MHP-A) was prepared as described above for 10-methacryloxydecyl phosphate (MDP-A from POCl$_3$), except that 1,6-hexanediol was substituted for 1,10-decanediol. Chemical characterization was by NMR analysis.

6-Methacryloxyhexyl Phosphate (MHP-B from P$_2$O$_5$)

6-Hydroxyhexyl Methacrylate Synthesis: 1,6-Hexanediol (1000.00 g, 8.46 mol, Sigma-Aldrich) was placed in a 1-liter 3-neck flask equipped with a mechanical stirrer and a narrow tube blowing dry air into the flask. The solid diol was heated to 90° C., at which temperature all the solid melted. With continuous stirring, p-toluenesulfonic acid crystals (18.95 g, 0.11 mol) followed by BHT (2.42 g, 0.011 mol) and methacrylic acid (728.49.02 g, 8.46 mol). Heating at 90° C. with stirring was continued for 5 hours during which time vacuum was applied using tap water aspirator for 5-10 minutes after each half-hour reaction time. The heat was turned off and the reaction mixture was cooled to room temperature. The viscous liquid obtained was washed with 10% aqueous sodium carbonate twice (2×240 ml), followed by washing with water (2×240 ml), and finally with 100 ml of saturated NaCl aqueous solution. The obtained oil was dried using anhydrous Na$_2$SO$_4$ then isolated by vacuum filtration to give 1067 g (67.70%) of 6-hydroxyhexyl methacrylate, a yellow oil. This desired product was formed along with 15-18% of 1,6-bis (methacryloyloxyhexane). Chemical characterization was by NMR analysis.

6-Methacryloxyhexyl Phosphate Synthesis: A slurry was formed by mixing P$_2$O$_5$ (178.66 g, 0.63 mol) and methylene chloride (500 ml) in a 1-liter flask equipped with a mechanical stirrer under N$_2$ atmosphere. The flask was cooled in an ice bath (0-5° C.) for 15 minutes. With continuous stirring, 6-hydroxyhexyl methacrylate (962.82 g, which contained 3.78 mol of the mono-methacrylate, along with its dimethacrylate by-product as described above) was added to the flask slowly over 2 hours. After complete addition, the mixture was stirred in the ice bath for 1 hour then at room temperature for 2 hours. BHT (500 mg) was added, and then the temperature was raised to reflux (40-41° C.) for 45 minutes. The heat was turned off and the mixture was allowed to cool to room temperature. The solvent was removed under vacuum to afford 1085 g (95.5%) of 6-Methacryloxyhexyl Phosphate (MHP-B) as a yellow oil. Chemical characterization was by NMR analysis.

Surface-Treated Zirconia (ZrO$_2$) Filler

Zirconia Sol (217.323 g; 23.5% solids; Nalco, Naperville, Ill.) was weighed into a plastic flask and then added slowly with vigorous stirring to a solution of mono-2-(methacryloyloxy)ethyl succinate (28.796 g; Sigma-Aldrich) in 1-methoxy-2-propanol (200.001 g; Sigma-Aldrich) that was contained in a plastic flask. The resulting mixture was then dried at 90° C. to powder form (dryness) in a convection oven and subsequently ground with a mortar and pestle to a fine powder form for easier later redispersion. Average primary particle size of the zirconia filler was approximately 5 nm, with 50-75 nm loose agglomerates.

Caprolactone methacrylate phosphate (CMA-P)

Caprolactone methacrylate phosphate was prepared as a derivative from caprolactone (Sigma-Aldrich) and HEMA followed by conversion of the hydroxyl group to a phosphate acid as described herein for other phosphate compounds. Chemical characterization was by NMR analysis.

HEMA-P (Mixture of HEMA Phosphates and tetraHEMA Pyrophosphate)

A 1-liter three-necked round-bottomed flask fitted with a reflux condenser with gas inlet, a mechanical stirrer, and an addition funnel with gas outlet was charged with 76.7g of POCl$_3$ and 500 ml THF. A solution of 130.5 g HEMA, 101.5 g triethylamine (TMA) and 87 g of THF was placed in the addition funnel. The flask was cooled via an ice-water-salt bath to approximately −5° C. The solution was added dropwise with stirring over a period of 25 minutes during which the temperature was maintained between 0° C. and −5° C. The mixture was stirred for three hours allowing the temperature to rise to room temperature. To the flask was added an additional 200 ml of THF to facilitate stirring. To the addition funnel was added a solution of 51 g of TEA and 6.8 g water in 50 ml of THF. After cooling the flask to 0-5° C. via the ice-water-salt bath, the solution was added dropwise during 16 minutes. The mixture was allowed to come to room temperature and stirred for 18 hours. The mixture was filtered to remove the precipitated salts and the THF removed in vaccuo. The product, 168g, was a light orange liquid which was characterized by $^1H$, $^{13}C$ and $^{31}P$ NMR to be a mixture of mono-, di-, and tri-HEMA phosphate and tetraHEMA pyrophosphate.

Examples 1-8

Self-Etching Adhesive Compositions

Non-aqueous, self-etching adhesive compositions (Examples 1-8) were prepared by combining the components in Table 1. Each composition included a polymerizable acid phosphate, other polymerizable components, a zirconia filler (nano-sized primary particles), a photoinitiator system, and optionally a polymerizable surfactant.

The adhesive coating was then dried and thinned using a gentle to moderate stream of air for about 5-10 seconds and cured for 10 seconds with an XL 3000 dental curing light. The shear bond strength to enamel and dentin surfaces was determined according to the Test Method described herein. Adhesive compositions (Examples 2-5) were mixed with 10% aqueous RN-50, applied to a tooth surface, and measured for enamel and dentin shear bond strength in a similar manner. Test results are provided in Table 2.

TABLE 2

Shear Bond Strength Results

| Run | Adhesive Composition | Shear Bond Strength to Enamel (MPa) (Std. Deviation) | Shear Bond Strength to Dentin (MPa) (Std. Deviation) |
| --- | --- | --- | --- |
| 1 | Example 1 | 18.0 (6.2) | 24.4 (3.2) |
| 2 | Example 2 | 21.5 (6.1) | 23.8 (7.5) |
| 3 | Example 3 | 16.9 (1.3) | 24.3 (3.7) |
| 4 | Example 4 | 21.9 (7.7) | 20.5 (4.3) |
| 5 | Example 5 | 16.9 (9.2) | 19.4 (3.3) |

The application procedure described above using Example 6 adhesive composition was repeated with 3 different operators to assess operator variability with the procedure. The results of shear bond strength testing are reported in Table 3.

TABLE 1

Adhesive Compositions (Examples 1-8)

| Components (Parts by Weight) | Ex. 1 | Ex. 2 | Ex. 3 | Ex. 4 | Ex. 5 | Ex. 6 | Ex. 7 | Ex. 8A | Ex. 8B |
| --- | --- | --- | --- | --- | --- | --- | --- | --- | --- |
| BisGMA | 26.09 | 26.09 | 26.09 | 26.09 | 26.09 | 26.26 | 25.89 | 25.75 | 23.54 |
| TEGDMA | 30.58 | 30.58 | 30.58 | 30.58 | 30.58 | 30.62 | 30.36 | 30.38 | 28.49 |
| HEMA | 15.28 | 15.28 | 15.28 | 15.28 | 15.28 | 15.24 | 15.06 | 15.12 | 6.43 |
| MHP-B | 12.29 | 0 | 0 | 0 | 0 | 12.18 | 13.18 | 4.03 | 8.22 |
| PM-2 | 0 | 12.29 | 0 | 0 | 0 | 0 | 0 | 8.16 | 17.29 |
| MDP-A | 0 | 0 | 12.29 | 0 | 0 | 0 | 0 | 0 | 0 |
| MDP-B | 0 | 0 | 0 | 12.29 | 0 | 0 | 0 | 0 | 0 |
| GDMA-P | 0 | 0 | 0 | 0 | 12.29 | 0 | 0 | 0 | 0 |
| ZrO$_2$ Filler | 13.38 | 13.38 | 13.38 | 13.38 | 13.38 | 13.32 | 13.18 | 13.20 | 12.31 |
| CPQ | 1.05 | 1.05 | 1.05 | 1.05 | 1.05 | 1.05 | 1.04 | 1.04 | 0.92 |
| EDMAB | 0.79 | 0.79 | 0.79 | 0.79 | 0.79 | 0.80 | 0.78 | 0.79 | 0.72 |
| DPIPF6 | 0.53 | 0.53 | 0.53 | 0.53 | 0.53 | 0.54 | 0.52 | 0.53 | 0.52 |
| RN-50 | 0 | 0 | 0 | 0 | 0 | 0 | 0 | 1.00 | 1.58 |
| Totals: | 100 | 100 | 100 | 100 | 100 | 100 | 100 | 100 | 100 |

Example 9

Application of Non-Aqueous Adhesive Composition+Water/Surfactant Diluent ("Wet-Brush Technique")

An adhesive test sample was prepared by dipping a dental application brush into a 10% by weight aqueous solution of NOIGEN RN-50 surfactant (subsequently referred to as "10% aqueous RN-50") and then mixing the wet brush tip with 2 drops (approximately 60 mg) of adhesive composition (Example 1). The resulting sample (30-60 mg) was applied to an air-dried bovine tooth surface (see Test Method described herein) and allowed to remain undisturbed for 20 seconds.

TABLE 3

| Run | Operator | Adhesive Composition | Shear Bond Strength to Enamel (MPa) | Shear Bond Strength to Dentin (MPa) |
| --- | --- | --- | --- | --- |
| 1 | A | Example 6 | 23.2 | 23.4 |
| 2 | B | Example 6 | 19.4 | 23.0 |
| 3 | C | Example 6 | 20.6 | 22.9 |
| | | Average: | 21.1 | 23.1 |

The application procedure described above using Example 6 adhesive composition was again repeated with 3 different operators, except that the 10% aqueous RN-50 was replaced by water only. The results of shear bond strength testing are reported in Table 4.

TABLE 4

| Run | Operator | Adhesive Composition | Shear Bond Strength to Enamel (MPa) | Shear Bond Strength to Dentin (MPa) |
|---|---|---|---|---|
| 1 | A | Example 6 | 14.7 | 13.9 |
| 2 | B | Example 6 | 20.4 | 19.0 |
| 3 | C | Example 6 | 13.3 | 11.1 |
|  |  | Average: | 16.1 | 14.7 |

Example 10

Application of Non-Aqueous Adhesive Composition+Water/Surfactant Diluent

A series of adhesive test samples were prepared by pre-mixing an adhesive composition (Example 7) with varying amounts (5-8% by weight) of 10% aqueous RN-50 surfactant. Each test sample (approximately 30-60 mg) was applied with a dental application brush to an air-dried tooth surface and measured for shear bond strength to enamel and dentin surfaces according to the Test Method described herein. Test results are provided in Table 5.

TABLE 5

| Run | Adhesive Composition | Added 10% Aqueous RN-50 (Weight %) | Shear Bond Strength to Enamel (MPa) (Std. Deviation) | Shear Bond Strength to Dentin (MPa) (Std. Deviation) |
|---|---|---|---|---|
| 1 | Example 7 | 5 | 11.7 (2.1) | 17.4 (3.9) |
| 2 | Example 7 | 6 | 15.5 (7.7) | 21.0 (2.7) |
| 3 | Example 7 | 7 | 17.4 (5.1) | 23.5 (3.4) |
| 4 | Example 7 | 8 | 21.4 (5.2) | 27.3 (5.9) |

Example 11

Application of Non-Aqueous Adhesive Composition (+Surfactant)+Water Diluent (Application to Air-Dried Tooth Surface)

A series of adhesive test samples were prepared by dipping a water-wet dental application brush (having approximately 8-9 mg of water) into varying amounts (1 drop/approx. 35 mg; 2 drops/approx. 70 mg; or 3 drops/approx. 105 mg) of an adhesive composition (Example 8A) containing 1.00% of RN-50 surfactant. Each test sample was applied with the brush to an air-dried bovine tooth enamel surface and rubbed with rapid agitation on the entire enamel surface for 20 seconds. The adhesive coating was then dried and thinned using a gentle to moderate stream of air for about 5-10 seconds and cured for 10 seconds with an XL 3000 dental curing light. The shear bond strength to enamel was determined according to the Test Method described herein. Test results are provided in Table 6.

TABLE 6

| Run | Adhesive Composition | Quantity of Added Adhesive Composition (mg) | Quantity of Added Water (mg) | Shear Bond Strength to Enamel (MPa) (Std. Deviation) |
|---|---|---|---|---|
| 1 | Example 8A | 35 | 8-9 | 22.0 (4.2) |
| 2 | Example 8A | 70 | 8-9 | 21.1 (4.2) |
| 3 | Example 8A | 105 | 8-9 | 25.4 (5.7) |

Example 12

Application of Non-Aqueous Adhesive Composition (+Surfactant) (Application to Tooth Surfaces with Varying Degrees of "Wetness")

A series of shear bond strength evaluations were made by applying a non-aqueous adhesive composition (Example 8A or Example 8B) that contained RN-50 surfactant to a tooth surface according to the Test Method described herein. Before application, the tooth surface was "dried" by one of the following 4 techniques: (1) air-dried to a "dry surface" with no visible (unaided, naked eye) amount of water present; (2) blot dried to a "slightly damp surface" from blotting with a KIMWIPE towel so that water was still visible on up to 50% of the tooth surface; (3) partially blot dried to a "damp surface" from blotting with a KIMWIPE towel so that water was still visible on the majority (greater than 50%) of the tooth surface; or (4) left completely flooded ("saturated" with no attempt to dry). For each evaluation, approximately 30-60 mg of the adhesive composition was applied to the tooth surface with a dental application brush and rubbed with rapid agitation on the entire tooth surface for 20 seconds. The adhesive coating was then dried and thinned using a gentle to moderate stream of air for about 5-10 seconds and cured for 10 seconds with an XL 3000 dental curing light. Optionally, a second application of the adhesive composition was made to the initial, dried adhesive coating (before curing) without agitation on the tooth surface. The adhesive coating was immediately cured for 10 seconds with an XL 3000 dental curing light and the shear bond strengths to enamel and dentin surfaces were determined according to the Test Method described herein. Test results are provided in Table 7 and are compared to results of evaluating SINGLE BOND total etch adhesive system (3M Company) used according to manufacturer's directions.

TABLE 7

| Run | Adhesive Comp. | Tooth Surface Condition | Application Method | Shear Bond Strength to Enamel (MPa) (Std. Deviation) | Shear Bond Strength to Dentin (MPa) (Std. Deviation) |
|---|---|---|---|---|---|
| 1 | Ex. 8A | Saturated | 1-Coat | 20.6 (8.2) | 19.8 (1.8) |
| 2 | Ex. 8A | Saturated | 2-Coats | 28.3 (9.9) | 28.0 (6.2) |

TABLE 7-continued

| Run | Adhesive Comp. | Tooth Surface Condition | Application Method | Shear Bond Strength to Enamel (MPa) (Std. Deviation) | Shear Bond Strength to Dentin (MPa) (Std. Deviation) |
|---|---|---|---|---|---|
| 3 | Ex. 8A | Damp | 1-Coat | 19.9 (4.8) | NT* |
| 4 | Ex. 8A | Damp | 2-Coats | NT | 26.1 (1.8) |
| 5 | Ex. 8A | Dry | 1-Coat | 11.7 (2.8) | NT |
| 6 | Ex. 8A | Saturated | 1-Coat | 24.1 (7.4) | NT |
| 7 | Ex. 8A | Saturated | 1-Coat | 25.6 (7.6) | NT |
| 8 | Ex. 8A | Slightly Damp | 1-Coat | 13.5 (1.6) | 19.5 (5.7) |
| 9 | Ex. 8B | Saturated | 2-Coats | 29.4 (6.3) | 37.1 (3.1) |
| 10 | SINGLE BOND Total Etch Adhesive System | | | 28.2 (4.0) | 24.4 (1.2) |

NT*—Not Tested

Examples 13-24

Self-Etching Adhesive Compositions (Water-in-Oil Emulsions)

Self-etching adhesive compositions (Examples 13-24) were prepared by combining the components as listed in Tables 8, 9 and 10. For each composition, water was added slowly as the last component to afford clear liquid samples that based on X-Ray Scattering evaluations (as described herein) were water-in-oil microemulsions. Each composition included a polymerizable acid phosphate, other polymerizable components, water, a photoinitiator system, and a polymerizable surfactant.

A series of shear bond strength evaluations were made by applying each adhesive composition (Examples 13-24) to a tooth surface according to the Test Method described herein. Before application, the tooth surface was air-dried to a "dry surface" with only trace amounts of water present.

For each evaluation, approximately 30-60 mg of the adhesive composition was applied to the tooth surface with a dental application brush and rubbed with rapid agitation on the entire tooth surface for 20 seconds. The adhesive coating was then dried and thinned using a gentle to moderate stream of air for about 5-10 seconds and cured for 10 seconds with an XL 3000 dental curing light. The shear bond strengths to enamel and dentin surfaces were determined according to the Test Method described herein and test results are provided in Tables 8, 9 and 10.

TABLE 8

Adhesive Compositions (Examples 13-16)

| Components (Parts by Weight) | Example 13 | Example 14 | Example 15 | Example 16 |
|---|---|---|---|---|
| MDP-A | 18.78 | 19.39 | 19.88 | 20.32 |
| UDMA | 14.23 | 14.69 | 15.06 | 15.40 |
| BisGMA | 7.12 | 7.34 | 7.53 | 7.70 |
| Ethyl Acetate | 12.94 | 13.35 | 13.69 | 14.00 |
| Water | 11.13 | 9.35 | 6.85 | 4.90 |
| HEMA | 28.46 | 29.37 | 30.13 | 30.79 |
| RN-50 | 2.59 | 2.67 | 2.74 | 2.80 |
| CPQ | 1.90 | 1.54 | 1.64 | 1.63 |
| EDMAB | 1.55 | 1.25 | 1.34 | 1.33 |
| DPIPF6 | 1.31 | 1.06 | 1.13 | 1.12 |
| Totals: | 100 | 100 | 100 | 100 |
| Shear Bond Strength to Enamel (MPa) (Std. Deviation) | 13.3 (1.6) | 12.3 (1.0) | 12.2 (3.6) | 10.5 (2.0) |
| Shear Bond Strength to Dentin (MPa) (Std. Deviation) | 12.1 (1.9) | 10.5 (1.5) | 10.8 (3.3) | 11.4 (2.1) |

TABLE 9

Adhesive Compositions (Examples 17-20)

| Components (Parts by Weight) | Example 17 | Example 18 | Example 19 | Example 20 |
|---|---|---|---|---|
| HEMA | 0 | 0 | 0 | 5.32 |
| Allyl Methacrylate | 10.65 | 21.30 | 0 | 0 |
| EGDM | 10.65 | 0 | 10.65 | 15.97 |
| DEGDM | 0 | 0 | 10.65 | 0 |
| PM-2 | 0 | 5.32 | 5.32 | 5.32 |
| EBECRYL 168 | 5.32 | 5.32 | 0 | 5.32 |
| MDP-B | 5.32 | 0 | 5.32 | 5.32 |
| BisGMA | 21.30 | 21.30 | 21.30 | 21.30 |
| TEGDMA | 15.97 | 15.97 | 15.97 | 10.65 |
| UDMA | 5.32 | 5.32 | 5.32 | 5.32 |
| Water | 5.32 | 5.32 | 5.32 | 5.32 |
| RN-50 | 10.65 | 10.65 | 10.65 | 10.65 |
| Ethyl Acetate | 5.32 | 5.32 | 5.32 | 5.32 |
| CPQ | 1.81 | 1.81 | 1.81 | 1.81 |
| EDMAB | 1.28 | 1.28 | 1.28 | 1.28 |
| DPIPF6 | 1.06 | 1.06 | 1.06 | 1.06 |
| Totals: | 100 | 100 | 100 | 100 |
| Shear Bond Strength to Enamel (MPa) (Std. Deviation) | 16.5 (5.9) | 4.9 (1.5) | 23.5 (4.6) | 11.4 (2.4) |
| Shear Bond Strength to Dentin (MPa) (Std. Deviation) | 16.0 (8.0) | 8.6 (5.3) | 14.5 (9.3) | 15.8 (6.8) |

TABLE 10

Adhesive Compositions (Examples 21-24)

| Components (Parts by Weight) | Example 21 | Example 22 | Example 23 | Example 24 |
|---|---|---|---|---|
| HEMA | 0 | 0 | 0 | 0 |
| Allyl Methacrylate | 9.18 | 0 | 0 | 0 |
| EGDM | 13.77 | 16.04 | 7.16 | 9.63 |
| DEGDM | 0 | 0 | 7.16 | 0 |
| PM-2 | 0 | 4.01 | 0 | 0 |
| EBECRYL 168 | 4.59 | 4.01 | 0 | 3.21 |
| MDP-B | 4.59 | 8.02 | 14.32 | 9.63 |
| BisGMA | 18.37 | 16.04 | 14.32 | 19.27 |
| TEGDMA | 18.37 | 24.06 | 25.05 | 19.27 |
| UDMA | 4.59 | 4.01 | 3.58 | 3.21 |
| Water | 4.59 | 4.01 | 3.58 | 6.42 |
| RN-50 | 9.18 | 8.02 | 7.16 | 12.85 |
| Ethyl Acetate | 9.18 | 8.02 | 14.32 | 12.85 |
| CPQ | 1.56 | 1.52 | 1.36 | 1.54 |
| EDMAB | 1.10 | 1.20 | 1.07 | 1.16 |
| DPIPF6 | 0.92 | 1.04 | 0.93 | 0.96 |
| Totals: | 100 | 100 | 100 | 100 |

| | OPERATOR: | | | | | | | |
|---|---|---|---|---|---|---|---|---|
| | A | B | A | B | A | B | A | B |
| Shear Bond Strength to Enamel (MPa) (Std. Deviation) | 15.2 (4.1) | 11.3 (3.2) | 15.0 (4.8) | 10.2 (1.6) | 11.9 (5.5) | 10.1 (2.4) | 14.5 (3.5) | 14.1 (4.4) |
| Shear Bond Strength to Dentin (MPa) (Std. Deviation) | 5.7 (3.7) | 13.8 (5.0) | 7.0 (4.6) | 10.5 (3.9) | 8.8 (3.8) | 8.2 (2.4) | 1.4 (3.1) | 8.3 (5.8) |

Evaluation of Adhesive Compositions Using X-ray Scattering Procedure

Adhesive compositions having different concentrations of water (Examples 13-16) were evaluated by an X-ray Scattering technique according to the following procedure:

Test samples were placed in a thin-walled quartz capillary cell. Small angle X-ray scattering (SAXS) data were collected in a transmission geometry using a Kratky camera, copper $K_\alpha$ radiation, and linear position sensitive detector registry of the scattered radiation. Data were accumulated for 60 minutes using a 30-micron incident beam slit. X-ray generator settings of 50 kV and 50 mA were employed.

The SAXS data indicate that the level of water present does modify the X-ray scattering at low angles in a manner consistent with the presence of a micelle structure. No evidence for the presence of a vesicle structure was observed. Concentration effects and ambiguity in assigning the correct background scatter can cause the absolute values calculated for radii of gyration ($R_G$) to have large errors associated with them. Relative relationships between $R_G$ values are found to be considerably more reliable. Data filenames, sample descriptions, and calculated radii of gyration are provided in Table 10A. Plots of the scattering data used for $R_G$ calculation and $R_G$ versus water content were also developed.

TABLE 10A

| Filename | Description | Water Content (%) | Radius of Gyration (Å) |
|---|---|---|---|
| 76601A | Example 13 (new) | 11.6 | 163.9 |
| 76601B | Example 14 (new) | 9.6 | 133.5 |
| 76601C | Example 15 (new) | 6.8 | 122.3 |
| 76601D | Example 16 (new) | 5.1 | 119.6 |
| 76601E | Example 13 (old) | 11.6 | 125.3 |
| 76601F | Example 14 (old) | 9.6 | 157.6 |
| 76601G | Example 15 (old) | 6.8 | 153.6 |
| 76601H | Example 16 (old) | 5.1 | 146.4 |

The data in Table 10A show that the adhesive compositions with water content ranging from about 12 to about 5 weight-% had average radii of droplets range from 16.4 nm to 12.0 nm (10 Å=1 nm) for "new" samples (about 1-week old) and range from 12.6 nm to 14.6 nm for "old" samples (greater than a month old). Such droplet sizes are well within the normally accepted value of water-in-oil microemulsion systems. It is therefore concluded that Examples 13-16 were water-in-oil microemulsions.

Examples 25-45

Self-Etching Adhesive Compositions (Water-in-Oil Emulsions)

Self-etching adhesive compositions (Examples 25-45) were prepared by combining the components as listed in Table 11. For each composition, water was added slowly as the last component to afford cloudy liquid samples that based on appearance, concentration of water, and separation behavior were considered to be water-in-oil emulsions. On standing, the liquid samples separated into a clear top aqueous layer and a cloudy bottom oil layer. On shaking, the liquid samples again took on a homogenous cloudy appearance. Each composition included a polymerizable acid phosphate, other polymerizable components, water, a photoinitiator system, and optionally a polymerizable surfactant.

A series of shear bond strength evaluations were made by applying each adhesive composition (Examples 25-45) to a tooth surface according to the Test Method described herein and as further described for Examples 13-24. Before application, the tooth surface was air-dried to a "dry surface" with only trace amounts of water present.

The shear bond strengths to dentin surfaces were determined according to the Test Method described herein and test results for initial (not aged) samples, samples aged 3 weeks at room temperature (approx. 23° C.), and samples aged 3 weeks at 45° C. are provided in Table 12.

TABLE 11

Components of Self-Etching Adhesive Compositions* (Parts by Weight)

| Example | TEGDMA | Water | AcAcMa | RN-50 | MDP-A | EtOAc | BisGMA | VBP |
|---|---|---|---|---|---|---|---|---|
| 25 | 35 | 10 | 14 | 0 | 11.8 | 7.8 | 19.7 | 1.6 |
| 26 | 20 | 25 | 10 | 4 | 11.8 | 7.8 | 19.7 | 1.6 |
| 27 | 20 | 14 | 20 | 5 | 11.8 | 7.8 | 19.7 | 1.6 |
| 28 | 26.3 | 16.33 | 14 | 2.33 | 11.8 | 7.8 | 19.7 | 1.6 |
| 29 | 29 | 10 | 20 | 0 | 11.8 | 7.8 | 19.7 | 1.6 |
| 30 | 20 | 19 | 20 | 0 | 11.8 | 7.8 | 19.7 | 1.6 |
| 31 | 34 | 10 | 10 | 5 | 11.8 | 7.8 | 19.7 | 1.6 |
| 32 | 23.1 | 20.66 | 12 | 3.16 | 11.8 | 7.8 | 19.7 | 1.6 |
| 33 | 35 | 14 | 10 | 0 | 11.8 | 7.8 | 19.7 | 1.6 |
| 34 | 24 | 10 | 20 | 5 | 11.8 | 7.8 | 19.7 | 1.6 |
| 35 | 20 | 25 | 14 | 0 | 11.8 | 7.8 | 19.7 | 1.6 |
| 36 | 24 | 25 | 10 | 0 | 11.8 | 7.8 | 19.7 | 1.6 |
| 37 | 30.16 | 13.16 | 12 | 3.66 | 11.8 | 7.8 | 19.7 | 1.6 |
| 38 | 23.16 | 15.16 | 17 | 3.66 | 11.8 | 7.8 | 19.7 | 1.6 |
| 39 | 27.66 | 13.16 | 17 | 1.16 | 11.8 | 7.8 | 19.7 | 1.6 |
| 40 | 23.16 | 17.66 | 17 | 1.16 | 11.8 | 7.8 | 19.7 | 1.6 |
| 41 | 30.66 | 13.16 | 14 | 1.16 | 11.8 | 7.8 | 19.7 | 1.6 |
| 42 | 30.66 | 15.16 | 12 | 1.16 | 11.8 | 7.8 | 19.7 | 1.6 |
| 43 | 25.16 | 13.16 | 17 | 3.66 | 11.8 | 7.8 | 19.7 | 1.6 |
| 44 | 25.16 | 20.66 | 12 | 1.16 | 11.8 | 7.8 | 19.7 | 1.6 |
| 45 | 26.33 | 16.33 | 14 | 2.33 | 11.8 | 7.8 | 19.7 | 1.6 |

*Each composition included a Photoinitiator System of that included the following Components (Parts by Weight): CPQ (1.6), EDMAB (1.3), and DPIPF6 (1.1).

TABLE 12

Average Shear Bond Strength (SBS) to Dentin (MPa)

| Example | Initial (No Aging) | Aged 3 weeks at 23° C. | Aged 3 weeks at 45° C. |
|---|---|---|---|
| 25 | 16.1 | 16.3 | 10.7 |
| 26 | 1.4 | 3.8 | 17 |
| 27 | 13.1 | 16.2 | 18.1 |
| 28 | 13.5 | 15.0 | 11.6 |
| 29 | 11.4 | 13.3 | 7.0 |
| 30 | 12.1 | 13.1 | 11.9 |
| 31 | 10.7 | 12.7 | 11.4 |
| 32 | 11.6 | 11.6 | 11.1 |
| 33 | 17.4 | 19.0 | 17.6 |
| 34 | 14.8 | 16.7 | 10.9 |
| 35 | 18.4 | 19.6 | 15.0 |
| 36 | 16.4 | 17.2 | 14.9 |
| 37 | 7.3 | 11.6 | 15.0 |
| 38 | 8.8 | 10.6 | 13.8 |
| 39 | 10.6 | 11.7 | 10.9 |

TABLE 12-continued

Average Shear Bond Strength (SBS) to Dentin (MPa)

| Example | Initial (No Aging) | Aged 3 weeks at 23° C. | Aged 3 weeks at 45° C. |
|---|---|---|---|
| 40 | 9.7 | 9.8 | 14.4 |
| 41 | 10.2 | 12.9 | 15.2 |
| 42 | 11.7 | 17.4 | 11.4 |
| 43 | 12.0 | 13.5 | 15.8 |
| 44 | 16.2 | 17.0 | 14.5 |
| 45 | 14.9 | 15.8 | 13.3 |

Examples 46-47

Self-Etching Adhesive Compositions (Water-in-Oil Emulsions)

Self-etching adhesive compositions (Examples 46 and 47) were prepared by combining the components as listed in Table 13 according to the following sequence:

1. Solution A and Solution B were prepared by combining the components listed.
2. Solutions A and B were mixed together with agitation.

Example 46 was a clear liquid considered to be a water-in-oil microemulsion, whereas Example 47 was a liquid milky in appearance and considered to be a water-in-oil macroemulsion. It is noted that the surfactant AOT-100 was used in the Solution B to prepare Example 46. This surfactant is well known to provide inverse micelles and thus Solution B used to prepare Example 46 was considered to be an inverse micelle system involving water droplets of micron or submicron size encapsulated by the surfactant.

A series of shear bond strength evaluations were made by applying each adhesive composition (Examples 46 and 47) to enamel and dentin surfaces according to the Test Method described herein and as described for Examples 13-24. Test results are provided in Table 13.

TABLE 13

Adhesive Compositions (Examples 46 and 47)

|  | Example 46 | | | Example 47 | | |
|---|---|---|---|---|---|---|
| Components | A (g) | B (g) | Parts by Wt. | A (g) | B (g) | Parts by Wt. |
| HEMA | 1 | | 12.09 | 1 | | 10.67 |
| BisGMA | 0.25 | | 3.02 | 0.25 | | 2.67 |
| Water | 2.5 | 0.5 | 36.26 | 0.5 | 0.15 | 6.93 |
| VBP | 0.1 | | 1.21 | 0.1 | | 1.07 |
| MDP-A | | | | | 2 | 21.33 |
| MHP-A | | 2 | 24.17 | | | |
| UDMA | | 0.5 | 6.04 | | 0.5 | 5.33 |
| AOT-100 | | 0.25 | 3.02 | | | |
| Ethyl Acetate | | 0.5 | 6.04 | | 4 | 42.67 |
| CPQ | | | 1.69 | | | 1.70 |
| EDMAB | | | 1.16 | | | 1.21 |
| DPIPF6 | | | 1.06 | | | 1.10 |
| RN-50 | 0.1 | | 1.21 | | 0.5 | 5.33 |
| LA 010 | 0.25 | | 3.02 | | | |
| Totals: | 4.3 | 3.75 | 100 | 1.85 | 7.15 | 100.00 |
| Shear Bond Strength to Enamel (MPa) (Std. Deviation) | | | 8.4 (3.3) | | | 18.2 (2.0) |
| Shear Bond Strength to Dentin (MPa) (Std. Deviation) | | | 13.4 (2.0) | | | 20.8 (1.0) |

Examples 48-55

Self-Etching Adhesive Compositions (Water-in-Oil Emulsions)

Self-etching adhesive compositions (Examples 48-55) were prepared by combining the components as listed in Table 14 according to the following sequence:

1. Solution A was prepared by emulsifying the water into the organic components.
2. Solution B was prepared by emulsifying the water/solvent into the organic components.
3. Solutions A and B were mixed together with agitation.
4. Neat RN-50 was mixed into the combined emulsions.
5. The photoinitiators (PI) were mixed into the combined emulsions.

The combined components of the resulting adhesive compositions (Examples 48-55) are listed in Table 15.

A series of shear bond strength evaluations were made by applying each adhesive composition (Examples 48-55) to enamel and dentin surfaces according to the Test Method described herein and as described for Examples 13-24. Test results are provided in Table 15.

TABLE 14

Adhesive Compositions (Examples 48-55)

| Components | A (g) | B (g) | A + B (g) | Added RN-50 (g) | Added PI (g) | Parts by Wt. (Total) |
|---|---|---|---|---|---|---|
| HEMA | 2.200 | | 2.200 | | | 20.95 |
| BisGMA | 0.550 | | 0.550 | | | 5.24 |
| Water | 1.100 | | 1.100 | | | 13.62 |
| VBP | 0.220 | | 0.220 | | | 2.10 |
| MDP (or MHP) | | 1.452 | 1.452 | | | 13.83 |
| Ethyl Acetate or TEGDMA | | 2.948 | 2.948 | | | 28.08 |
| Water | | 0.330 | 0.330 | | | |
| UDMA | | 1.100 | 1.100 | | | 10.48 |
| RN-50 | | | | 0.2 | | 1.90 |
| CPQ | | | | | 0.16 | 1.52 |
| EDMAB | | | | | 0.13 | 1.24 |
| DPIPF6 | | | | | 0.11 | 1.05 |
| Totals: | 4.070 | 5.830 | 9.900 | 0.2 | 0.40 | 100 |

TABLE 15

Adhesive Compositions (Examples 48-55)

| Components (Parts by Weight) | Ex. 48 | Ex. 49 | Ex. 50 | Ex. 51 | Ex. 52 | Ex. 53 | Ex. 54 | Ex. 55 |
|---|---|---|---|---|---|---|---|---|
| HEMA | 20.95 | 20.95 | 20.95 | 20.95 | 20.95 | 20.95 | 20.95 | 20.95 |
| BisGMA | 5.24 | 5.24 | 5.24 | 5.24 | 5.24 | 5.24 | 5.24 | 5.24 |

TABLE 15-continued

Adhesive Compositions (Examples 48-55)

| Components (Parts by Weight) | Ex. 48 | Ex. 49 | Ex. 50 | Ex. 51 | Ex. 52 | Ex. 53 | Ex. 54 | Ex. 55 |
|---|---|---|---|---|---|---|---|---|
| Water | 13.62 | 13.62 | 13.62 | 13.62 | 13.62 | 13.62 | 13.62 | 13.62 |
| VBP | 2.10 | 2.10 | 2.10 | 2.10 | 2.10 | 2.10 | 2.10 | 2.10 |
| MDP-A | 13.83 | | | | 13.83 | | | |
| MDP-B | | 13.83 | | | | 13.83 | | |
| MHP-A | | | 13.83 | | | | 13.83 | |
| MHP-B | | | | 13.83 | | | | 13.83 |
| Ethyl Acetate | 28.08 | 28.08 | 28.08 | 28.08 | | | | |
| TEGDMA | | | | | 28.08 | 28.08 | 28.08 | 28.08 |
| UDMA | 10.48 | 10.48 | 10.48 | 10.48 | 10.48 | 10.48 | 10.48 | 10.48 |
| RN-50 | 1.90 | 1.90 | 1.90 | 1.90 | 1.90 | 1.90 | 1.90 | 1.90 |
| CPQ | 1.52 | 1.52 | 1.52 | 1.52 | 1.52 | 1.52 | 1.52 | 1.52 |
| EDMAB | 1.24 | 1.24 | 1.24 | 1.24 | 1.24 | 1.24 | 1.24 | 1.24 |
| DPIPF6 | 1.05 | 1.05 | 1.05 | 1.05 | 1.05 | 1.05 | 1.05 | 1.05 |
| Totals: | 100 | 100 | 100 | 100 | 100 | 100 | 100 | 100 |
| Shear Bond Strength to Enamel (MPa) (Std. Deviation) | 16.5 (3.0) | 12.7 (1.6) | 10.9 (1.8) | 10.1 (1.5) | 9.8 (4.6) | 10.7 (4.4) | 11.8 (2.7) | 12.1 (3.0) |
| Shear Bond Strength to Dentin (MPa) (Std. Deviation) | 16.0 (1.7) | 15.3 (2.5) | 12.1 (4.3) | 6.4 (1.8) | 9.7 (2.3) | 12.4 (3.9) | 15.5 (5.5) | 15.0 (5.0) |

Examples 56-57

Self-Etching Adhesive Compositions (Water-in-Oil Emulsions)

Self-etching adhesive compositions (Examples 56 and 57) were prepared by combining the components as listed in Table 16. Example 56 was a non-aqueous composition that included a polymerizable acid phosphate, other polymerizable components, a photoinitiator system, and a polymerizable surfactant. Example 57 was identical to Example 56, except that water (3.4%) was added as described for Examples 13-24 to form a clear liquid microemulsion.

Shear bond strength evaluations were made by applying each adhesive composition (Examples 56 and 57) to a tooth surface according to the Test Method described herein. Before application, the tooth surface was slightly wet (visible water present on up to 50% of the tooth surface).

For each evaluation, approximately 60 mg of the adhesive composition was applied to the tooth surface with a dental application brush and rubbed with rapid agitation on the entire tooth surface for 20 seconds. The adhesive coating was then dried and thinned using a gentle to moderate stream of air for about 3-5 seconds. A second coat of the adhesive was applied to the first coating and (for Example 57 only) air-dried as for the first adhesive coating. The coatings were then cured for 10 seconds with an XL 3000 dental curing light and the shear bond strengths to enamel and dentin surfaces were determined according to the Test Method described herein. Test results are provided in Table 16.

The procedure was repeated for Example 57, except that added water was placed on the tooth surface with a dental application brush prior to application of the adhesive composition. Shear bond strength results were 15.4 (1.9) MPa for enamel and 18.1 (11.7) MPa for dentin.

TABLE 16

Adhesive Compositions (Examples 56 and 57)

| Components (Parts by Weight) | Example 56 | Example 57 |
|---|---|---|
| NPGDMA | 9.1 | 8.8 |
| TEGDMA | 24.3 | 23.5 |
| BisGMA | 30.5 | 29.4 |
| MHP | 17.7 | 17.1 |
| RN-50 | 4.7 | 4.5 |
| EtOAc | 9.0 | 8.7 |
| CPQ | 2.0 | 1.9 |
| EDMAB | 1.3 | 1.3 |
| DPI | 1.4 | 1.3 |
| Water | | 3.4 |
| Totals: | 100 | 100 |
| Shear Bond Strength to Enamel (MPa) (Std. Deviation) | 14.6 (3.4) | 15.2 (8.1) |
| Shear Bond Strength to Dentin (MPa) (Std. Deviation) | Not Evaluated | Not Evaluated |

Example 58

Evaluation of Various Photoinitiator and Electron Donor Compounds

Resin A

Resin A was prepared by combining TEGDMA (24.93 parts), BisEMA6 (24.93 parts), HEMA-P (49.85 parts), and BHT (0.30 parts) to afford a homogeneous composition.

Resin B

Resin B was prepared by combining TEGDMA (24.85 parts), BisEMA6 (24.85 parts), HEMA-P (49.70 parts), CPQ (0.30 parts), and BHT (0.30 parts) to afford a homogeneous composition.

Various photoinitiator and electron donor compounds were combined with either Resin A or Resin B and the resulting composition evaluated for curing according to the Curing Test Method described herein. The photoinitiator and electron donor compounds, their concentration and solubility observations in the resins, and the curing results are provided in Table 17. The studies were repeated with DPIPF6 (1 part) added to the compositions and the curing results were essentially identical to the results without added DPIPF6.

TABLE 17

Curing Results of Resins Containing Various Initiator and Electron Donor Compounds

| Compound | Physical State of Compound | Compound Concentration in Resin | Solubility/ Miscibility Observations | Curing Result |
|---|---|---|---|---|
| IRGACURE 819 | Solid | 2% in Resin A | Dissolved | YES |
| MOST | Solid | 2% in Resin A | Cloudy | YES |
| DMAPE | Solid | 2% in Resin B | Dissolved | NO |
| DHEPT | Solid | 2% in Resin B | Dissolved | NO |
| EDMAB | Solid | 2% in Resin B | Dissolved | YES |
| 4-DMAB | Liquid | 2% in Resin B | Not totally soluble | YES (soft) |
| t-BDMA | Liquid | 2% in Resin B | Miscible | NO |
| DMA | Solid | 2% in Resin B | Miscible | YES |
| DMABN | Solid | 2% in Resin B | Dissolved | YES |
| DMABA | Solid | 2% in Resin B | Dissolved | YES (soft) |
| 3-DMAB | Solid | 2% in Resin B | Not totally soluble | NO |
| 4-DMABn | Solid | 2% in Resin B | Not totally soluble | NO |
| TEAB | Solid | 2% in Resin B | Dissolved | NO |
| N-PhG | Solid | 2% in Resin B | Not totally soluble | NO |
| N-PhGEE | Liquid | 2% in Resin B | Dissolved | YES (soft) |
| DMAEMA | Liquid | 2% in Resin B | Miscible | NO |
| TEA | Solid | 2% in Resin B | Miscible | NO |
| ATU | Liquid | 2% in Resin B | Dissolved | NO |

Examples 59-66

Self-Adhesive Compositions

Examples 59-66 were prepared by combining the components in Table 18 according to the following general procedure: The curable ethylenically unsubstituted components were mixed to form a uniform phase. Subsequently, the initiator system components were added with mixing to a homogeneous state. Finally, the fillers and other components were added and thoroughly dispersed to afford a homogeneous paste composition.

Examples 59-66 were evaluated for Storage Stability according to the Test Method described herein and the results are provided in Table 18. Examples 59 and 61-65 were evaluated for Compression Strength, Diametral Tensile Strength, and Adhesion to Enamel and Dentin according to the Test Methods described herein and the results are provided in Table 18. All Examples tested had adhesive strength to "untreated enamel" of greater than 9 MPa and to "untreated dentin" of greater than 3 MPa.

TABLE 18

Compositions and Evaluation Results of Examples 59-66

| Components (Parts by Weight) | Ex. 59 | Ex. 60 | Ex. 61 | Ex. 62 | Ex. 63 | Ex. 64 | Ex. 65 | Ex. 66 |
|---|---|---|---|---|---|---|---|---|
| TEGDMA | 6.9 | 6.9 | 6.1 | 6.9 | 9.1 | 6.9 | 10.6 | 0 |
| BisEMA6 | 6.9 | 6.9 | 0 | 0 | 9.1 | 6.9 | 10.6 | 10.6 |
| BisGMA | 0 | 0 | 6.1 | 6.9 | 0 | 0 | 0 | 0 |
| PEG 400 DMA | 0 | 0 | 0 | 0 | 0 | 0 | 0 | 10.6 |
| GDMA-P | 13.8 | 13.8 | 12.1 | 13.8 | 0 | 0 | 0 | 0 |
| MH-P | 0 | 0 | 0 | 0 | 0 | 0 | 3.0 | 3.0 |
| CMA-P | 0 | 0 | 0 | 0 | 6.1 | 0 | 0 | 0 |
| HEMA-P | 0 | 0 | 0 | 0 | 0 | 13.8 | 0 | 0 |
| BHT | 0.1 | 0.1 | 0.1 | 0.1 | 0.1 | 0.1 | 0.1 | 0.1 |
| 4-DMAB | 0 | 0.7 | 0 | 0 | 0 | 0 | 0 | 0 |
| EDMAB | 0.7 | | 0.6 | 0.7 | 0.6 | 0.7 | 0.6 | 0.6 |
| CPQ | 0.1 | 0.1 | 0.1 | 0.1 | 0.1 | 0.1 | 0.1 | 0.1 |
| DPIPF6 | 0 | 0 | 0.1 | 0 | 0 | 0 | 0 | 0.1 |
| Zr-Si Filler | 69 | 69 | 74.9 | 71.6 | 74.9 | 69 | 75 | 75 |
| AEROSIL R812S | 2.6 | 2.6 | 0 | 0 | 0 | 2.6 | 0 | 0 |
| EYB | 0 | 0 | 0 | 0 | 0 | 0 | 0 | 0.01 |
| Total: | 100 | 100 | 100 | 100 | 100 | 100 | 100 | 100 |
| Evaluation Results: | | | | | | | | |
| Storage Stability (Days at 45° C.) | >94 | >94 | >66 | >91 | >93 | >92 | 29 | 37 |
| CS (MPa) | 421 | NT* | 457 | 435 | 337 | 414 | 369 | NT |
| DTS (MPa) | 88 | NT | 82 | 89 | 698 | 83 | 76 | NT |
| Adhesion to Enamel (MPa) (Before aging) | 13.6 | NT | 11.4 | 10.5 | 9.8 | 12.0 | 17.7 | NT |
| Adhesion to Dentin (MPa) (Before aging) | 3.8 | NT | 5.3 | 5.6 | 5.2 | 4.9 | 4.9 | NT |
| Adhesion to Enamel (MPa) (After aging 1 month/45° C.) | NT | NT | NT | NT | NT | NT | 16.6 | NT |

TABLE 18-continued

Compositions and Evaluation Results of Examples 59-66

| Components (Parts by Weight) | Ex. 59 | Ex. 60 | Ex. 61 | Ex. 62 | Ex. 63 | Ex. 64 | Ex. 65 | Ex. 66 |
|---|---|---|---|---|---|---|---|---|
| Adhesion to Enamel (MPa) (After aging 3 months/45° C.) | NT | NT | NT | NT | NT | 9.7 | NT | NT |
| Adhesion to Dentin (MPa) (After aging 3 months/45° C.) | NT | NT | NT | NT | NT | 4.2 | NT | NT |

*= Not Tested

Comparative Example 1

Comparative Example 1 (reported as Example 3 in International Publication WO 02/092021 (Hecht et al.)) was prepared in a similar manner to Examples 59-66 by combining the following components to afford a homogeneous paste composition: TEGDMA (6 parts), GDMA-P (13.5 parts), EDMAB (0.4 parts), CPQ (0.04 parts), AEROSIL R-812S (5 parts), $Ca(OH)_2$ (1 part), Photac FAS (74 parts), and $Cu(OAc)_2$ (1 part). Comparative Example 1 was evaluated for Storage Stability according to the Test Method described herein and found to have a storage stability of less than 3 days at 45° C. and 90% RH.

Example 67

Self-Adhesive Composition—Orthodontic Direct Bonding Method

Self-adhesive composition Example 61 was modified by increasing the level of Zr—Si Filler from 74.9 to 83.0 parts by weight (and decreasing proportionately the level of the other components) to afford self-adhesive Example 67 that was evaluated as an orthodontic adhesive in the following orthodontic direct bonding procedure.

Bovine teeth were mounted in acrylic denture base material so that the labial surfaces were exposed. The mounted teeth were cleaned with slurry of pumice in water and rinsed. The moist teeth (i.e., wet teeth with water visible on teeth) were treated according to either a Control Protocol or an Invention Protocol as follows:

(1) Control Protocol. TRANSBOND Plus Self Etching Primer (SEP, 3M Unitek, Monrovia, Calif.) was applied to teeth by rubbing in a circular motion for 3 seconds followed by blowing with oil-free compressed air. TRANSBOND XT orthodontic adhesive (3M Unitek, Monrovia, Calif.) was applied via syringe to the bonding base of 10 different VICTORY SERIES brackets (3M Unitek, p/n 017-401). Each bracket was pressed in place on a tooth and excess flash was cleaned from the periphery of the bonding base.

(2) Invention Protocol. Self-adhesive composition (orthodontic adhesive) Example 67 was applied via syringe to the bonding base of 10 different VICTORY SERIES brackets. Each bracket was pressed in place on a tooth and excess flash was cleaned from the periphery of the bonding base.

After allowing to sit for 60 seconds, each bracket was illuminated for 3 seconds mesial and 3 seconds distal with an ORTHO Lite plasma arc curing light (3M Unitek). The bonded brackets were then stored in 37° C. water for 24 hours. The bonded brackets were removed from the water and mounted with the gingival tie wings pointing vertically in a test fixture attached to an INSTRON 4204 testing machine. A 0.020-inch diameter standard round wire (3M Unitek, p/n 211-200) was looped under the occlusal tie wings and attached to the crosshead of the testing machine. After moving the crosshead to make the wire snug, it was set to move at 0.2 inches/minute until the bracket was debonded. The peak force required to debond the bracket was recorded, divided by the bonding base area, and defined as the bond strength. Bond Strength results were reported as the average of the 10 measurements and were as follows:

(1) Control Protocol: Average Bond Strength=18.0 MPa (2) Invention Protocol: Average Bond Strength=10.6 MPa Example 68

Self-Adhesive Composition—Orthodontic Indirect Bonding Method

Self-adhesive composition Example 61 was modified by not including the DPIPF6 component (0.1 parts by weight) to afford self-adhesive Example 68 that was evaluated as an orthodontic adhesive in the following orthodontic indirect bonding procedure. (For indirect bonding, a lower viscosity adhesive (Example 68) was chosen to reduce the necessity of cleaning flash after tray seating.)

Bovine teeth were mounted in acrylic denture base material so that the labial surfaces were exposed. Two coats of PA 0810 (polyvinyl alcohol solution, PTM&W Industries, Inc., Santa Fe Springs, Calif.) were applied (as a "separating layer") to each tooth and dried. A bracket with TRANSBOND XT orthodontic adhesive was pressed onto each tooth, the flash cleaned, and the adhesive cured with a 3-second illumination from the mesial and distal sides with an ORTHO Lite curing light. A dab of MEMOSIL 2 bite register material (Heraeus Kulzer GmBH & Co., Hanau, Germany) was placed over each bracket, pressed into place with a mixing pad sheet, and allowed to cure. Each bracket, now encapsulated in MEMOSIL, was removed from its respective tooth. Each tooth was cleaned with a slurry of pumice in water and each bracket base was cleaned by agitation with a toothbrush under running water. All teeth were rinsed before bonding. The moist teeth (i.e., wet teeth with water visible on teeth) were treated according to either a Control Protocol or an Invention Protocol as follows:

(1) Control Protocol. TRANSBOND Plus Self Etching Primer was applied to the teeth by rubbing in a circular motion for 3 seconds followed by blowing with oil-free compressed air. ORTHO SOLO orthodontic primer (Ormco, Orange, Calif.) was applied to the bonding base of 5 brackets prepared in the steps above, drying with oil-free compressed air after each application. Each bracket was pressed in place on a tooth using the MEMOSIL as a locator.

(2) Invention Protocol. Self-adhesive composition (orthodontic adhesive) Example 68 was applied via syringe to the bonding base of 5 brackets prepared in the steps above, drying with oil-free compressed air after each application. Each bracket was pressed in place on a tooth using the MEMOSIL as a locator.

For both Protocols, after allowing the brackets to sit for 60 second, the orthodontic adhesives were cured using an ORTHO Lite curing light with a 20-second illumination on each of the mesial and distal sides of the brackets. The MEMOSIL was then removed from the brackets. The bonded brackets were then stored in 37° C. water for 24 hours. The bonded brackets were removed from the water and evaluated for bond strength as described for Example 67. Bond Strength results were reported as the average of the 5 measurements and were as follows:

(1) Control Protocol: Average Bond Strength=22.4 MPa
(2) Invention Protocol: Average Bond Strength=9.5 MPa The complete disclosure of all patents, patent applications, and publications, and electronically available material cited herein are incorporated by reference. The foregoing detailed description and examples have been given for clarity of understanding only. No unnecessary limitations are to be understood there from. The invention is not limited to the exact details shown and described, for variations obvious to one skilled in the art will be included within the invention defined by the claims.

What is claimed is:

1. A method of restoring a dental structure, the method comprising:
    applying an aqueous diluent to an unetched dental structure surface to provide a wet, unetched dental structure surface;
    applying a non-aqueous, self-adhesive composition to the wet, unetched dental structure surface; and
    hardening the non-aqueous, self-adhesive composition under conditions effective to form a bond between the hardened composition and the dental structure;
    wherein the aqueous diluent comprises an acid sensitive dye, an antibacterial agent, a water soluble monomer, a pH adjuster agent, a buffer, a stabilizer, a surfactant, a fluoride anion, a fluoride releasing agent, or combinations thereof.

2. The method of claim 1 wherein the aqueous composition comprises a water soluble monomer.

3. The method of claim 2 wherein the non-aqueous, self-adhesive composition comprises an ethylenically unsaturated compound with acid functionality, an ethylenically unsaturated compound without acid functionality, a filler, and an initiator system.

4. The method of claim 3 wherein the non-aqueous self-adhesive composition comprises at least 40% by weight filler.

5. The method of claim 3 wherein the acid functionality comprises carboxylic acid functionality, phosphoric acid functionality, phosphonic acid functionality, sulfonic acid functionality, or combinations thereof.

6. The method of claim 2 wherein the dental structure surface comprises enamel, dentin, or cementum.

7. The method of claim 6 wherein the bond strength is at least 7 MPa.

8. The method of claim 1 wherein the non-aqueous, self-adhesive composition comprises an ethylenically unsaturated compound with acid functionality, an ethylenically unsaturated compound without acid functionality, a filler, and an initiator system.

9. The method of claim 8 wherein the non-aqueous self-adhesive composition comprises at least 40% by weight filler.

10. The method of claim 8 wherein the acid functionality comprises carboxylic acid functionality, phosphoric acid functionality, phosphonic acid functionality, sulfonic acid functionality, or combinations thereof.

11. The method of claim 1 wherein the dental structure surface comprises enamel, dentin, or cementum.

12. The method of claim 11 wherein the bond strength is at least 7 MPa.

* * * * *

UNITED STATES PATENT AND TRADEMARK OFFICE
CERTIFICATE OF CORRECTION

PATENT NO. : 7,632,098 B2
APPLICATION NO. : 10/916240
DATED : December 15, 2009
INVENTOR(S) : Afshin Falsafi It is certified that error appears in the above-identified patent and that said Letters Patent is hereby corrected as shown below:

Column 2
Page 2, Line 6, delete "Occurence," and insert -- Occurrence," --, therefor.
Page 3, Lines 23-24, delete "Gerneral Informatio," and insert -- General Information, --, therefor.

Column 9
Line 16, delete "hexacrylate," and insert -- hexaacrylate, --, therefor.
Line 17, delete "bis[l-(3-" and insert -- bis[1-(3- --, therefor.

Column 10
Line 47, delete "methyl-1-phenylpropane-1-one" and insert -- methyl-1-phenylpropan-1-one --, therefor.

Column 17
Line 30, delete "Baneijee" and insert -- Banerjee --, therefor.

Column 22
Line 27, delete "sulfocuccinate" and insert -- sulfosuccinate --, therefor.
Line 38, delete "Fluoroaluminasilicate" and insert -- Fluoroaluminosilicate --, therefor.

Column 44
Line 6, Claim 3, delete "claim 2" and insert -- claim 1 --, therefor.
Line 17, Claim 6, delete "claim 2" and insert -- claim 1 --, therefor.

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,632,098 B2  Page 1 of 1
APPLICATION NO. : 10/916240
DATED : December 15, 2009
INVENTOR(S) : Falsafi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 391 days.

Signed and Sealed this

Second Day of November, 2010

David J. Kappos
*Director of the United States Patent and Trademark Office*